(12) United States Patent
Takasuka et al.

(10) Patent No.: US 9,354,516 B2
(45) Date of Patent: May 31, 2016

(54) RESIST COMPOSITION

(71) Applicant: Mitsubishi Gas Chemical Company, Inc., Tokyo (JP)

(72) Inventors: Masaaki Takasuka, Kanagawa (JP); Masatoshi Echigo, Kanagawa (JP); Yu Okada, Okayama (JP); Yumi Ochiai, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 14/436,170

(22) PCT Filed: Oct. 16, 2013

(86) PCT No.: PCT/JP2013/078104
§ 371 (c)(1),
(2) Date: Apr. 16, 2015

(87) PCT Pub. No.: WO2014/061710
PCT Pub. Date: Apr. 24, 2014

(65) Prior Publication Data
US 2015/0286136 A1    Oct. 8, 2015

(30) Foreign Application Priority Data
Oct. 17, 2012   (JP) ................................. 2012-229482

(51) Int. Cl.
| | | |
|---|---|---|
| *G03F 7/004* | (2006.01) | |
| *G03F 7/027* | (2006.01) | |
| *C07C 39/17* | (2006.01) | |
| *G03F 7/038* | (2006.01) | |
| *H01L 21/027* | (2006.01) | |

(52) U.S. Cl.
CPC ............... *G03F 7/027* (2013.01); *C07C 39/17* (2013.01); *G03F 7/004* (2013.01); *G03F 7/038* (2013.01); *G03F 7/0382* (2013.01); *H01L 21/027* (2013.01); *C07C 2101/14* (2013.01); *C07C 2103/92* (2013.01)

(58) Field of Classification Search
CPC ....... G03F 7/004; G03F 7/0045; G03F 7/038; G03F 7/039; C07C 39/17
USPC ............... 430/270.1, 322, 913, 927; 568/745
See application file for complete search history.

(56) References Cited

U.S. PATENT DOCUMENTS

| | | | | |
|---|---|---|---|---|
| 8,110,334 B2 * | 2/2012 | Echigo | ................... | C07C 37/20 430/270.1 |
| 8,883,937 B2 * | 11/2014 | Echigo | ................... | C07C 69/21 430/270.1 |
| 9,122,153 B2 * | 9/2015 | Echigo | ................... | C07C 39/17 |
| 2008/0153031 A1 | 6/2008 | Echigo et al. | | |
| 2011/0020756 A1 | 1/2011 | Bozano et al. | | |
| 2013/0078569 A1 * | 3/2013 | Jain | ................... | C07C 67/29 430/270.1 |
| 2013/0157195 A1 * | 6/2013 | Green | ................... | C07C 69/753 430/281.1 |

FOREIGN PATENT DOCUMENTS

| | | |
|---|---|---|
| JP | H11-322656 A | 11/1999 |
| JP | 2003-313546 A | 11/2003 |
| JP | 2003-321423 A | 11/2003 |
| JP | 2005-326838 A | 11/2005 |
| JP | 2008-145539 A | 6/2006 |
| JP | 2007-197389 A | 8/2007 |
| JP | 2008-116677 A | 5/2008 |
| JP | WO 2008053974 A1 * 5/2008 ............. C07C 37/20 |
| JP | 2009-173623 A | 8/2009 |
| JP | 2010-277061 A | 12/2010 |
| JP | 2011-28270 A | 2/2011 |
| JP | 2011-81200 A | 4/2011 |
| JP | 2013-140342 A | 7/2013 |
| WO | 2011-037073 A1 | 3/2011 |

OTHER PUBLICATIONS

"A New Three-Component Photoresist Based on Calix[4] resorcinarene Derivative, a Cross-linker, and a Photo-acid Generator" by Tomonari Nakayama, Masayoshi Nomura, Kohji Haga and Mitsuru Ueda; Yamagata University; 1998 The Chemical Society of Japan; Received May 18, 1998.

International Search Report dated Jan. 14, 2014, for PCT/JP2013/078104 and English translation of the same (8 pages).

Rumbolt, G. et al., "Rational Synthesis of Resorcarenes with Alternating Substituents at Their Bridging Methine Carbons", The Journal of Orgnic Chemistry, pp. 9618-9619.

Abis, L. et al., "Structurally New Macrocycles from the Resorcinol-Aldehyde Condensation. Configurational and Conformational Analyses by Means of Dynamic NMR, NOE, and T1 Experiments", The Journal of Organic Chemistry, pp. 5475-5479.

Abis, L. et al., "Nuclear Magnetic Resonance Elucidation of Ring-Inversion Processes Elucidation of Ring-Inversion Processes in Macrocyclic Octaols", Journal of the Chemical Society, pp. 2075-2080.

\* cited by examiner

*Primary Examiner* — Amanda C Walke

(74) *Attorney, Agent, or Firm* — Fitch Even Tabin & Flannery LLP

(57) ABSTRACT

A resist composition of the present invention is a resist composition containing a resist base material and a solvent. The resist base material contains a specific stereoisomer. A content of the specific stereoisomer in the resist base material is 50 to 100% by mass.

17 Claims, No Drawings

RESIST COMPOSITION

CROSS-REFERENCE TO RELATED APPLICATIONS

This application is a U.S. national phase application filed under 35 U.S.C. §371 of International Application PCT/JP2013/078104, filed on Oct. 16, 2013, designating the United States, which claims priority from Japanese Application Number 2012-229482, filed Oct. 17, 2012, which are hereby incorporated herein by reference in their entirety.

TECHNICAL FIELD

The present invention relates to a resist composition containing a specific stereoisomer, and a method for producing a resist pattern.

BACKGROUND ART

Conventional typical resist materials are polymeric resist materials capable of forming amorphous thin films. A line pattern of about 45 to 100 nm is formed by irradiating a resist thin film made by coating a substrate with a solution of a polymeric resist material such as polymethyl methacrylate, polyhydroxy styrene with an acid dissociation reactive group, or polyalkyl methacrylate with ultraviolet, far ultraviolet, electron beam, extreme ultraviolet (EUV), and X-ray or the like.

However, polymeric resist materials have a molecular weight as large as about 10,000 to 100,000 and also wide molecular weight distribution. Therefore, in lithography using a polymeric resist material, roughness occurs on a fine pattern surface; the pattern dimension becomes difficult to be controlled; and the yield decreases. Therefore, there is a limitation in miniaturization of a pattern with lithography using a conventional polymeric resist material. Then, in order to make a finer pattern, various low molecular weight resist materials have been proposed.

As a low molecular weight resist material candidate, for example, an alkaline development type negative type radiation-sensitive composition (For example, see Japanese Patent Application Laid-Open No. 2005-326838 and Japanese Patent Application Laid-Open No. 2008-145539) using a low molecular weight polynuclear polyphenol compound as a main component has been suggested.

As another low molecular weight resist material candidate, for example, an alkaline development type negative type radiation-sensitive composition using a low molecular weight cyclic polyphenol compound (For example, see Patent Document 3 and Non Patent Document 1) as a main component has been suggested.

SUMMARY OF INVENTION

However, the negative type radiation-sensitive compositions described in Japanese Patent Application Laid-Open No. 2005-326838 and Japanese Patent Laid-Open No. 2008-145539 have insufficient heat resistance, which may provide the poor shape of the resulting resist pattern.

The low molecular weight cyclic polyphenol compound described in Japanese Patent Laid-Open No. 2009-173623 and Non Patent Document T. Nakayama, M. Nomura, K. Haga, M. Ueda: Bull. Chem. Soc. Jpn., 71, 2979 (1998) is expected to provide a resist pattern with small molecular size, high resolution and small roughness due to its low molecular weight. Furthermore, the low molecular weight cyclic polyphenol compound provides high heat resistance even with the low molecular weight, by having a rigid cyclic structure in its backbone.

However, the currently known low molecular weight cyclic polyphenol compound has low solubility in a safe solvent used for a semiconductor production process. The alkaline development type negative type radiation-sensitive composition using such a low molecular weight cyclic polyphenol compound as a main component has low sensitivity, which may provide the poor shape of the resulting resist pattern. Therefore, an improvement in the low molecular weight cyclic polyphenol compound has been desired. The low molecular weight cyclic phenol compound described in Japanese Patent Laid-Open No. 2009-173623 provides a resist pattern having a good shape. However, substance characteristics such as solubility characteristics are slightly unstable, which does not stably provide a resist pattern having a good shape.

Then, the object of the present invention is to provide a resist composition which has high sensitivity, and stably provides a resist pattern having small roughness and a good shape.

The inventors have, as a result of devoted examinations to solve the above problems, found out a specific stereoisomer having significantly improved solubility in a safe solvent. Furthermore, the inventors have surprisingly found out that a resist composition using the specific stereoisomer as an acid amplification type low molecular resist base material has high sensitivity, and can stably provide a resist pattern having small roughness and a better shape, and reached the present invention.

More specifically, the present invention is as follows.
1. A resist composition comprising a resist base material and a solvent,
wherein the resist base material comprises a compound represented by the following formula (1):

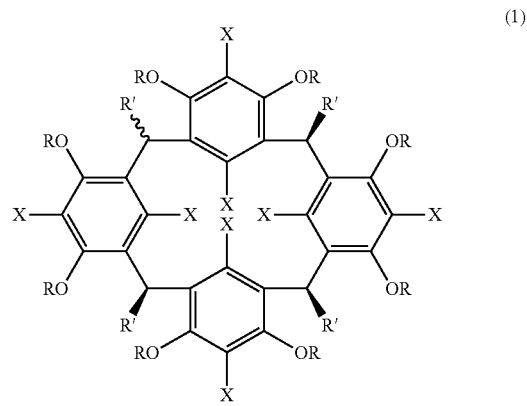

wherein R are each independently a hydrogen atom, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group);

R' and X are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 20 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 20 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group); and directions of three R' to a direction of one R' in a 16-membered plane are cis, cis, and trans directions in order of clockwise rotation, and a content of the compound represented by the formula (1) in the resist base material is 50 to 100% by mass.

2. The resist composition according to the above [1], wherein X is a hydrogen atom, a hydroxyl group, or a substituted or non-substituted alkoxy group having 1 to 20 carbon atoms in the formula (1).

3. The resist composition according to the above [1], wherein, in the formula (1), R' is a group represented by the following formula (2), and X is the hydrogen atom:

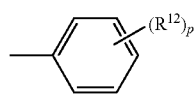

(2)

wherein p is an integer of 0 to 4; and $R^{12}$ are each independently a cyano group, a nitro group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, or a group represented by the following formula (3):

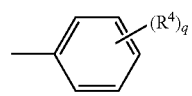

(3)

wherein $R^4$ are each independently a cyano group, a nitro group, a substituted or non-substituted heterocyclic group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, a substituted or non-substituted aryl group having 6 to 14 carbon atoms, a substituted or non-substituted alkoxy group having 1 to 14 carbon atoms, or a substituted or non-substituted alkylsilyl group having 1 to 14 carbon atoms; and q is an integer of 0 to 5.

4. The resist composition according to the above [1], wherein, in the formula (1), R' is a group represented by the following formula (4), and R and X are a hydrogen atom:

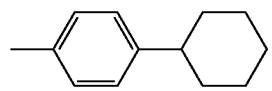

(4)

5. The resist composition according to any one of the above [1] to [4], wherein a content of the solvent is 20 to 99% by mass, and a content of a component other than the solvent is 1 to 80% by mass.

6. The resist composition according to any one of the above [1] to [5], further comprising an acid generating agent (C) which directly or indirectly generates acid upon exposure to any one radiation selected from the group consisting of visible light, ultraviolet, excimer laser, electron beam, extreme ultraviolet (EUV), X-ray, and ion beam.

7. The resist composition according to any one of the above [1] to [6], further comprising an acid crosslinking agent (G).

8. The resist composition according to any one of the above [1] to [7], further comprising an acid diffusion controlling agent (E).

9. The resist composition according to any one of the above [1] to [8], wherein the component other than the solvent comprises the resist base material (A), an acid generating agent (C), an acid crosslinking agent (G), and an acid diffusion controlling agent (E), and based on a total content of 100 parts by mass of the component other than the solvent, a content of the resist base material (A) is 50.000 to 99.498 parts by mass; a content of the acid generating agent (C) is 0.001 to 49.000 parts by mass; a content of the acid crosslinking agent (G) is 0.500 to 49.000 parts by mass; and a content of the acid diffusion controlling agent (E) is 0.001 to 49.000 parts by mass.

10. The resist composition according to any one of the above [1] to [9], wherein the resist composition can form an amorphous film by spin coating.

11. The resist composition according to the above [10], wherein a dissolution rate of the amorphous film into a developing solution at 23° C. is 10 angstrom/sec or more.

12. The resist composition according to the above [10], wherein a dissolution rate of the amorphous film into a developing solution is 5 angstrom/sec or less after exposed to KrF excimer laser, extreme ultraviolet, electron beam, or X-ray, or after heated at 20 to 250° C.

13. A method for producing a resist pattern, comprising the steps of:
coating a substrate with the resist composition according to any one of the above [1] to [12], thereby forming a resist film;
exposing the resist film; and
developing the exposed resist film.

14. A compound represented by the following formula (1):

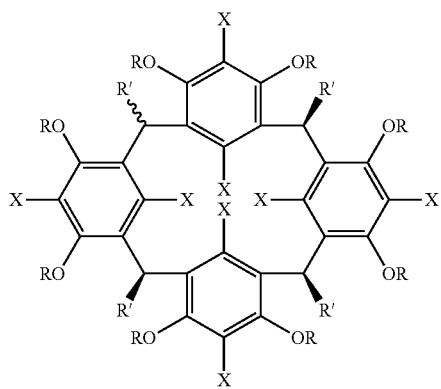

(1)

wherein R are each independently a hydrogen atom, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group);

R' and X are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 20 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 20 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group); and directions of three R' to a direction of one R' in a 16-membered plane are cis, cis, and trans directions in order of clockwise rotation.

15. The compound according to the above [14], wherein X is a hydrogen atom, a hydroxyl group, or a substituted or non-substituted alkoxy group having 1 to 20 carbon atoms in the formula (1).

16. The compound according to the above [14], wherein, in the formula (1), R' is a group represented by the following formula (2), and X is the hydrogen atom:

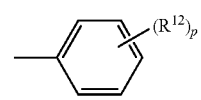

(2)

wherein p is an integer of 0 to 4; and
$R^{12}$ are each independently a cyano group, a nitro group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, or a group represented by the following formula (3):

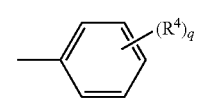

(3)

wherein $R^4$ are each independently a cyano group, a nitro group, a substituted or non-substituted heterocyclic group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, a substituted or non-substituted aryl group having 6 to 14 carbon atoms, a substituted or non-substituted alkoxy group having 1 to 14 carbon atoms, or a substituted or non-substituted alkylsilyl group having 1 to 14 carbon atoms; and q is an integer of 0 to 5.

17. The compound according to the above [14], wherein, in the formula (1), R' is a group represented by the following formula (4), and R and X are a hydrogen atom:

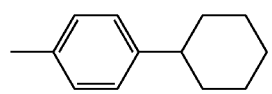

(4)

The present invention can provide a specific stereoisomer which has high solubility in a safe solvent, a resist composition which has high sensitivity and provides a resist pattern having small roughness and a good shape, and a resist pattern production method using the composition.

Hereinafter, an embodiment of the present invention (hereinafter, also referred to as "present embodiment") will be described in detail. The following embodiment is given in order to illustrate the present invention. The present invention is not limited to only the embodiment.

Compound Represented by the Formula (1)

The compound of the present embodiment is a compound which is represented by the following formula (1):

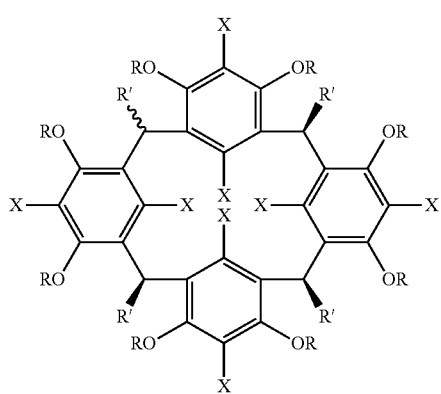

(1)

wherein R are each independently a hydrogen atom, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group);

R' and X are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 20 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 20 carbon atoms, a substituted or non-substituted alkylsilyl group having 1 to 20 carbon atoms, or a group in which each of the groups is bonded to a bivalent group (one or more groups selected from the group consisting of a substituted or non-substituted alkylene group, a substituted or non-substituted allylene group, and an ether group); and directions of three R' to a direction of one R' in a 16-membered plane are cis, cis, and trans directions in order of clockwise rotation.

As described above, the compound represented by the above formula (1) is a specific stereoisomer in which directions of three R' to a direction of one R' in a 16-membered plane are cis, cis, and trans directions in order of clockwise rotation (hereinafter, described also as a "cct body"). In the present embodiment, in a resist composition to be described below, a component containing such a specific stereoisomer (the compound represented by the above formula (1)) is used as a resist base material. Since such a specific stereoisomer (the compound represented by the above formula (1)) has high solubility in a safe solvent, the resist composition using the resist base material containing the compound represented by the above formula (1) as a main component can have high sensitivity, and stably provide a resist pattern having small roughness and a good shape.

The compound represented by the above formula (1) is one specific stereoisomer of four stereoisomers capable of being constituted by a calix compound represented by the following formula (Z).

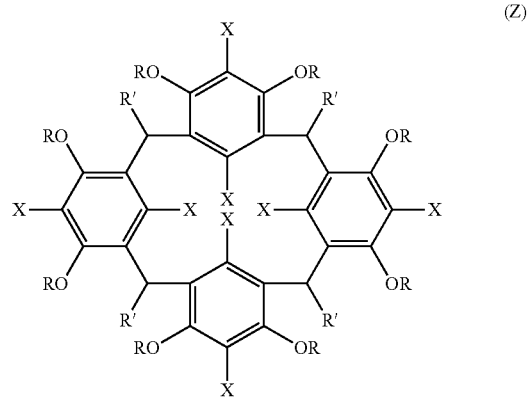

(Z)

In the formula (Z), R, R', and X are the same as R, R', and X in the formula (1).

The compound represented by the above formula (Z) is a 16-membered oligomer in which benzene rings each having two RO form a ring structure via a methine group or a methylene group at para positions of two RO. Therefore, since each of four R' has upward and downward bindings to the 16-membered plane, cis-trans isomers (stereoisomers) are present for each of the bindings. Therefore, in the compound represented by the above formula (Z), four stereoisomers are present as stereoisomers capable of being constituted by a compound having the same chemical formula. That is, the four stereoisomers are a (ccc) body, a (ctt) body, a (cct) body, and a (tct) body, as described below.

The (ccc) body is a compound having a steric structure where directions of three R' to a direction of one R' in the 16-membered plane in the above formula (Z) are cis, cis, and cis directions in order of clockwise rotation.

The (ctt) body is a compound having a steric structure where directions of three R' to a direction of one R' in the 16-membered plane in the above formula (Z) are cis, trans, and trans directions in order of clockwise rotation.

The (cct) body is a compound having a steric structure where directions of three R' to a direction of one R' in the 16-membered plane in the above formula (Z) are cis, cis, and trans directions in order of clockwise rotation (hereinafter, referred to as the "(cct) body" in some cases).

The (tct) body is a compound having a steric structure where directions of three R' to a direction of one R' in the 16-membered plane in the above formula (Z) are trans, cis, and trans directions in order of clockwise rotation.

From the point of increasing the heat resistance and sensitivity of the resist composition, in the formula (1), X is preferably a hydrogen atom, a hydroxyl group, or a substituted or non-substituted alkoxy group having 1 to 20 carbon atoms. In particular, in the formula (1), R' is more preferably a group represented by the following formula (2), and X is more preferably a hydrogen atom.

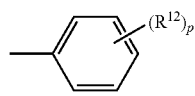

(2)

wherein p is an integer of 0 to 4; and

R12 are each independently a cyano group, a nitro group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, or a group represented by the following formula (3):

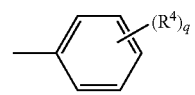

(3)

wherein R4 are each independently a cyano group, a nitro group, a substituted or non-substituted heterocyclic group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, a substituted or non-substituted aryl group having 6 to 14 carbon atoms, a substituted or non-substituted alkoxy group having 1 to 14 carbon atoms, or a substituted or non-substituted alkylsilyl group having 1 to 14 carbon atoms; and q is an integer of 0 to 5.

That is, the compound of the present embodiment is preferably a specific stereoisomer ((cct) body) represented by the following formula (1-1):

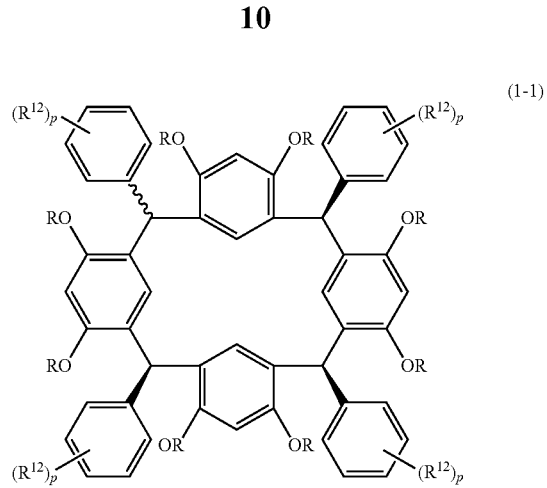

(1-1)

In the formula (1-1), R and $R^{12}$ are synonymous with R and $R^{12}$ described above. By using the resist base material containing such a specific stereoisomer as a main component, the heat resistance and sensitivity of the obtained resist composition tend to be improved.

From the point of increasing the heat resistance and sensitivity of the resist composition, in the formula (1), R' is more preferably a group represented by the following formula (4):

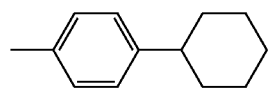

(4)

and, R and X are more preferably a hydrogen atom.

That is, the compound of the present embodiment is preferably a specific stereoisomer ((cct) body) represented by the following formula (1-2):

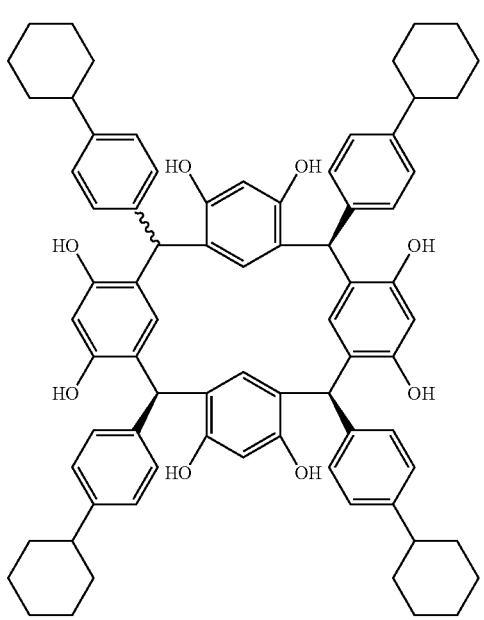

(1-2)

By using the resist base material containing such a specific stereoisomer as a main component, the heat resistance and sensitivity of the obtained resist composition tend to be further improved.

Unless the circumstances are exceptional, "substitution" in the present specification means that one or more hydrogen atoms in a functional group are substituted with a halogen atom, a hydroxyl group, a cyano group, a nitro group, a heterocyclic group, a linear aliphatic hydrocarbon group of 1 to 20 carbon atoms, a branched aliphatic hydrocarbon group of 3 to 20 carbon atoms, a cyclic aliphatic hydrocarbon group of 3 to 20 carbon atoms, an aryl group of 6 to 20 carbon atoms, an aralkyl group of 7 to 30 carbon atoms, an alkoxy group of 1 to 20 carbon atoms, an amino group of 0 to 20 carbon atoms, an alkenyl group of 2 to 20 carbon atoms, an acyl group of 1 to 20 carbon atoms, an alkoxycarbonyl group of 2 to 20 carbon atoms, an alkyloyloxy group of 1 to 20 carbon atoms, an aryloyloxy group of 7 to 30 carbon atoms, or an alkylsilyl group of 1 to 20 carbon atoms.

Examples of the non-substituted heterocyclic group include, but not particularly limited to, a pyridyl group, a bipyridyl group, a pyrrolidyl group, a pyrazolyl group, an imidazolyl group, an isoxazolyl group, an isothiazolyl group, a piperidyl group, a piperazyl group, a morpholyl group, a thiomorpholyl group, a triazole group, and a tetrazole group.

Examples of the substituted heterocyclic group include, but not particularly limited to, an N-methylpyridyl group, an N-fluoropyridyl group, an N-hydroxypyridyl group, an N-cyanopyridyl group, a methylbipyridyl group, a methylpyrrolidyl group, a methylpyrazolyl group, a methylimidazolyl group, a methylisoxazolyl group, a methylisothiazolyl group, a methylpiperidyl group, a methylpiperazyl group, a methylmorpholyl group, a methylthiomorpholyl group, a methyltriazole group, and a methyltetrazole group.

Examples of the non-substituted linear aliphatic hydrocarbon group of 1 to 20 carbon atoms include, but not particularly limited to, a methyl group, an ethyl group, a propyl group, a butyl group, a pentyl group, a hexyl group, an octyl group, a decyl group, a dodecyl group, a hexadecyl group, and an octadecyl group.

Examples of the substituted linear aliphatic hydrocarbon group of 1 to 20 carbon atoms include, but not particularly limited to, a fluoromethyl group, a 2-hydroxyethyl group, a 3-cyanopropyl group, and a 20-nitrooctadecyl group.

Examples of the non-substituted branched aliphatic hydrocarbon group of 3 to 20 carbon atoms include, but not particularly limited to, an isopropyl group, an isobutyl group, a tertiary-butyl group, a neopentyl group, a 2-hexyl group, a 2-octyl group, a 2-decyl group, a 2-dodecyl group, a 2-hexadecyl group, and a 2-octadecyl group.

Examples of the substituted branched aliphatic hydrocarbon group of 3 to 20 carbon atoms include, but not particularly limited to, a 1-fluoroisopropyl group and a 1-hydroxy-2-octadecyl group.

Examples of the non-substituted cyclic aliphatic hydrocarbon group of 3 to 20 carbon atoms include, but not particularly limited to, a cyclopropyl group, a cyclobutyl group, a cyclopentyl group, a cyclohexyl group, a cyclooctyl group, a cyclodecyl group, a cyclododecyl group, a cyclohexadecyl group, and a cyclooctadecyl group.

Examples of the substituted cyclic aliphatic hydrocarbon group of 3 to 20 carbon atoms include, but not particularly limited to, a 2-fluorocyclopropyl group and a 4-cyanocyclohexyl group.

Examples of the non-substituted aryl group of 6 to 20 carbon atoms include, but not particularly limited to, a phenyl group and a naphthyl group.

Examples of the substituted aryl group of 6 to 20 carbon atoms include, but not particularly limited to, a 4-isopropylphenyl group, a 4-cyclohexyl phenyl group, a 4-methylphenyl group and a 6-fluoronaphthyl group.

Examples of the non-substituted aralkyl group of 7 to 30 carbon atoms include, but not particularly limited to, a 4-methylphenyl group, a 4-ethylphenyl group, a 6-methylnaphthyl group, and a 2,6-dimethylnaphthyl group.

Examples of the substituted aralkyl group of 7 to 30 carbon atoms include, but not particularly limited to, a 4-fluoro-3-methylphenyl group.

Examples of the non-substituted alkoxy group of 1 to 20 carbon atoms include, but not particularly limited to, a methoxy group, an ethoxy group, a propoxy group, a butoxy group, a pentyloxy group, a hexyloxy group, an octyloxy group, a decyloxy group, a dodecyloxy group, a hexadecyloxy group, and an octadecyloxy group.

Examples of the substituted alkoxy group of 1 to 20 carbon atoms include, but not particularly limited to, a chloromethoxy group and a bromoethoxy group.

Examples of the non-substituted amino group of 0 to 20 carbon atoms include, but not particularly limited to, an amino group, a methylamino group, a dimethylamino group, an ethylamino group, a diethylamino group, a dipropylamino group, and a dibutylamino group.

Examples of the substituted amino group of 0 to 20 carbon atoms include, but not particularly limited to, a chloromethylamino group and a dibromomethylamino group.

Examples of the non-substituted alkenyl group of 2 to 20 carbon atoms include, but not particularly limited to, a vinyl group, a propynyl group, a butynyl group, a pentynyl group, a hexynyl group, an octynyl group, a decynyl group, a dodecynyl group, a hexadecynyl group, and an octadecynyl group.

Examples of the substituted alkenyl group of 2 to 20 carbon atoms include, but not particularly limited to, a chloropropynyl group.

Examples of the non-substituted acyl group of 1 to 20 carbon atoms include, but not particularly limited to, a formyl group, an acetyl group, a propanoyl group, a butanoyl group, a pentanoyl group, a hexanoyl group, an octanoyl group, a decanoyl group, a dodecanoyl group, a hexadecanoyl group, and a benzoyl group.

Examples of the substituted acyl group of 1 to 20 carbon atoms include, but not particularly limited to, a chloroacetyl group.

Examples of the non-substituted alkoxycarbonyl group of 2 to 20 carbon atoms include, but not particularly limited to, a methoxycarbonyl group, an ethoxycarbonyl group, a propoxycarbonyl group, a butoxycarbonyl group, a pentyloxycarbonyl group, a hexyloxycarbonyl group, an octyloxycarbonyl group, a decyloxycarbonyl group, a dodecyloxycarbonyl group, and a hexadecyloxycarbonyl group.

Examples of the substituted alkoxycarbonyl group of 2 to 20 carbon atoms include, but not particularly limited to, a chloromethoxycarbonyl group.

Examples of the non-substituted alkyloyloxy group of 1 to 20 carbon atoms include, but not particularly limited to, a methoxycarbonyloxy group, an ethoxycarbonyloxy group, a propoxycarbonyloxy group, a butoxycarbonyloxy group, a pentyloxycarbonyloxy group, a hexyloxycarbonyloxy group, an octyloxycarbonyloxy group, a decyloxycarbonyloxy group, a dodecyloxycarbonyloxy group, and a hexadecyloxycarbonyloxy group.

Examples of the substituted alkyloyloxy group of 1 to 20 carbon atoms include, but not particularly limited to, a chloromethoxycarbonyloxy group.

Examples of the non-substituted aryloyloxy group of 7 to 30 carbon atoms include, but not particularly limited to, a benzoyloxy group and a naphthylcarbonyloxy group.

Examples of the substituted aryloyloxy group of 7 to 30 carbon atoms include, but not particularly limited to, a chlorobenzoyloxy group.

Examples of the non-substituted alkylsilyl group of 1 to 20 carbon atoms include, but not particularly limited to, a methylsilyl group, an ethylsilyl group, a propylsilyl group, a butylsilyl group, a pentylsilyl group, a hexylsilyl group, an octylsilyl group, a decylsilyl group, a dodecylsilyl group, a hexadecylsilyl group, and an octadecylsilyl group.

Examples of the substituted alkylsilyl group of 1 to 20 carbon atoms include, but not particularly limited to, a chloromethylsilyl group.

The molecular weight of the compound represented by the formula (1) (cct body) is preferably 500 to 5000, more preferably 800 to 2000, and still more preferably 1000 to 2000. When the molecular weight is within the above range, the resist composition containing the resist base material containing the cct body as a main component improves the resolution while maintaining the film forming property required for a resist.

The glass transition temperature of the compound represented by the formula (1) (cct body) is preferably 100° C. or more, more preferably 120° C. or more, still more preferably 140° C. or more, and particularly preferably 150° C. or more. Although the upper limit of the glass transition temperature is not particularly limited, the upper limit is 300° C., for example. By having the glass transition temperature within the above range, the resist composition containing the resist base material containing the cct body as a main component, in a semiconductor lithography process, has heat resistance capable of maintaining the pattern shape, and improved performance such as high resolution.

The crystallization heat generation amount obtained by differential scanning calorimetrical analysis of the glass transition temperature of the compound represented by the formula (1) (cct body) is preferably less than 20 J/g. In the compound represented by the formula (1) (cct body), (crystallization temperature)–(glass transition temperature) is preferably 70° C. or more, more preferably 80° C. or more, still more preferably 100° C. or more, and particularly preferably 130° C. or more. Although the upper limit of (crystallization temperature)–(glass transition temperature) is not particularly limited, the upper limit is 200° C., for example. When the crystallization heat generation amount in the compound represented by the formula (1) (cct body) is less than 20 J/g or (crystallization temperature)–(glass transition temperature) is within the above range, by spin coating with the resist composition containing the resist base material containing the cct body as a main component, an amorphous film is easily formed; the film forming property required for a resist can be maintained over an extended period of time; and the resolution is further improved.

In the present embodiment, the crystallization heat generation amount, the crystallization temperature, and the glass transition temperature can be obtained by differential scanning calorimetrical analysis (DSC) using DSC/TA-50WS manufactured by Shimadzu Corporation as follows. About 10 mg of the sample is placed in a non-sealed container made of aluminum, and the temperature is raised to the melting point or more at the rate of temperature rise of 20° C./min in a nitrogen gas stream (50 mL/min). After quenching the sample, again the temperature is raised to the melting point or more at the rate of temperature rise of 20° C./min in a nitrogen gas stream (30 mL/min). After further quenching the sample, again the temperature is raised to 400° C. at the rate of temperature rise of 20° C./min in a nitrogen gas stream (30 mL/min). In the obtained DSC curve, the temperature at the middle point of the step of the baseline stepwisely changed (where the specific heat is changed into the half) is defined as the glass transition temperature (Tg), and the temperature at the subsequently appearing heat generation peak is defined as the crystallization temperature. Also, the heat generation amount is obtained from the area of the region surrounded by the heat generation peak and the baseline, as the crystallization heat generation amount.

The compound represented by the formula (1) (cct body) preferably has a low sublimation property under normal pressure at 100° C., preferably 120° C., more preferably 130° C., still more preferably 140° C., and particularly preferably 150° C. The low sublimation property means that the weight decrease after being kept at a predetermined temperature for 10 minutes in thermogravimetrical analysis is 10% or less, preferably 5% or less, more preferably 3% or less, still more preferably 1% or less, and particularly preferably 0.1% or less. Contamination of an exposure equipment by outgas upon exposure can be prevented by the low sublimation property of the compound represented by the formula (1) (cct body). The resist composition containing the resist base material containing such a cct body as a main component can have low line edge roughness (LER) and provide a good pattern shape.

The compound represented by the formula (1) (cct body) preferably meets F<3.0 (F represents total atom number/ (total carbon atom number–total oxygen atom number)), more preferably F<2.5, and still more preferably F<2.0. Although the lower limit of F is not particularly limited, the lower limit is 1.5, for example. When F meets the above condition, the resist composition containing the resist base material containing the cct body as a main component has excellent dry etching resistance.

The compound represented by the formula (1) (cct body) has high solubility in a safe solvent. Examples of the safe solvent include, but not particularly limited to, at least one solvent selected from the group consisting of propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate.

The compound represented by the formula (1) (cct body) dissolves in a solvent showing the highest dissolving ability to the compound among the above safe solvents in preferably 1% by mass or more, more preferably 5% by mass or more, and still more preferably 10% by mass or more at 23° C. Particularly, the compound represented by the formula (1) (cct body) dissolves in a solvent showing the highest dissolving ability to the compound among solvents selected from the group consisting of PGMEA, PGME, and CHN in preferably 20% by mass or more at 23° C. Furthermore, the compound represented by the formula (1) (cct body) particularly preferably dissolves in PGMEA in 20% by mass or more at 23° C. When the compound represented by the formula (1) (cct body) has the above solubility, the use of the resist composition containing the resist base material containing the cct body as a main component in a semiconductor production process in the actual production becomes possible.

A crosslinking reactive group initiating a crosslinking reaction by visible light, ultraviolet, excimer laser, electron beam, extreme ultraviolet (EUV), X-ray, and ion beam irradiation or a chemical reaction induced thereby may be introduced into the compound represented by the formula (1) (cct body), within the range of not deteriorating the effect of the present invention. Examples of a method for introducing the crosslinking reactive group into the compound represented by the formula (1) (cct body) include, but not particularly limited to, a method for reacting the compound with the crosslinking reactive group introducing agent in the presence of a basic catalyst. Examples of the crosslinking reactive group include, but not particularly limited to, a carbon-carbon multiple bond, an epoxy group, an azide group, a halogenated phenyl group, and a chloromethyl group. Examples of the crosslinking reactive group introducing agent include, but not particularly limited to, an acid having such a crosslinking reactive group, acid chloride, acid anhydride, a carboxylic acid derivative such as dicarbonate, and alkyl halide. A resist composition containing a compound having a crosslinking reactive group is also useful as a nonpolymeric resist composition with high resolution, high heat resistance, and solvent solubility.

A nonacid dissociation functional group may be introduced into at least one phenolic hydroxyl group of the compound represented by the formula (1) (cct body), within the range of not deteriorating the effect of the present invention. The nonacid dissociation functional group refers to a characteristic group not cleaving in the presence of an acid or not generating an alkali soluble group. Examples of the nonacid dissociation functional group include, but not particularly limited to, a functional group selected from the group consisting of an alkyl group of C1 to 20, a cycloalkyl group of C3 to 20, an aryl group of C6 to 20, an alkoxyl group of C1 to 20, a cyano group, a nitro group, a hydroxyl group, a heterocyclic group, halogen, a carboxyl group, alkylsilane of C1 to 20, and a derivative thereof, which are not degraded by action of an acid.

A naphthoquinone diazide ester group may be introduced into the phenolic hydroxyl group of the compound represented by the formula (1) (cct body), within the range of not deteriorating the effect of the present invention. A compound having a naphthoquinone diazide ester group introduced into at least one phenolic hydroxyl group of the compound can be used as a main component of a negative type resist composition. Moreover, the compound can be used as a main component of a positive type resist composition, and can be added to a resist composition, as an acid generating agent and an additive agent.

An acid generating functional group generating an acid by irradiation of radiation may be introduced into at least one phenolic hydroxyl group of the compound represented by the formula (1) (cct body), within the range of not deteriorating the effect of the present invention. The compound having the acid generating functional group introduced into at least one phenolic hydroxyl group of the compound can be used as a main component of a negative type resist composition. Moreover, the compound can be added to a resist composition as an additive agent.

Preferably, the compound represented by the above formula (1) (cct body) can form an amorphous film by spin coating. The compound can be applied to a typical semiconductor production process.

The compound represented by the above formula (1) (cct body) is useful as a negative type resist base material which becomes a hardly soluble compound in a developing solution by being irradiated with KrF excimer laser, extreme ultraviolet, electron beam, or X-ray. This is considered to be because by irradiating the compound with KrF excimer laser, extreme ultraviolet, electron beam, or X-ray, a condensation reaction among the compounds is induced to provide a compound hardly soluble in an alkaline developing solution. A resist pattern thus obtained has very small LER.

Method for Producing Compound Represented by Formula (1)

Although the compound represented by the above formula (1) (cct body) is not particularly limited, the compound is obtained by a condensation reaction of one or more compounds selected from the group consisting of aldehyde compounds (A1) with one or more compounds selected from the group consisting of phenolic compounds (A2), for example.

Preferably, the aldehyde compound (A1) has a monovalent group containing 1 to 4 formyl groups and has 2 to 59 carbon atoms; and the phenolic compound (A2) has 1 to 3 phenolic hydroxyl groups and has 6 to 15 carbon atoms.

The aldehyde compound (A1) has 2 to 59 carbon atoms. The aldehyde compound (A1) has a monovalent group containing 1 to 4 formyl groups. The aldehyde compound (A1) is selected from an aromatic aldehyde compound (A1A) and an aliphatic aldehyde compound (A1B). The aromatic aldehyde compound (A1A) is preferably a benzaldehyde compound of 7 to 24 carbon atoms. Examples of the benzaldehyde compound having 7 to 24 carbon atoms include, but not particularly limited to, benzaldehyde having a substituent group containing at least one alicyclic or aromatic ring in addition to an aromatic ring of benzaldehyde and having 7 to 24 carbon atoms. Specific examples of such benzaldehyde include, but not particularly limited to, methylbenzaldehyde, ethylbenzaldehyde, propylbenzaldehyde, butylbenzaldehyde, cyclopropylbenzaldehyde, cyclobutanebenzaldehyde, cyclopentanebenzaldehyde, cyclohexanebenzaldehyde, phenylbenzaldehyde, naphthylbenzaldehyde, adamanthylbenzaldehyde, norbornylbenzaldehyde, and lactylbenzaldehyde. Above all, propylbenzaldehyde, cyclohexylbenzaldehyde, and phenylbenzaldehyde are preferable, and propylbenzaldehyde and cyclohexylbenzaldehyde are more preferable. The aromatic aldehyde compound (A1A) may have a linear or branched alkyl group of 1 to 4 carbon atoms, a cyano group, a hydroxyl group, and a halogen or the like, within the range of not deteriorating the effect of the present invention. The aromatic aldehyde compound (A1A) may be used alone or in combination of two or more kinds. The aliphatic aldehyde compound (A1B) may have a cyano group, a hydroxyl group, and a halogen or the like, within the range of not deteriorating the effect of the present invention. The aliphatic aldehyde compound (A1B) may be used alone or in combination of two or more kinds.

The phenolic compound (A2) preferably has 6 to 15 carbon atoms. The phenolic compound (A2) preferably has 1 to 3 phenolic hydroxyl groups. Specific examples of the phenolic compound (A2) include, but not particularly limited to, phenol, catechol, resorcinol, hydroquinone, pyrogallol, 3-methoxy phenol, 3-ethoxy phenol, 3-cyclohexyloxy phenol, 1,3-dimethoxy benzene, 1,3-diethoxy benzene, and 1,3-dicyclohexyloxy benzene. Above all, resorcinol, pyrogallol, 3-methoxy phenol, 3-ethoxy phenol, 3-cyclohexyloxy phenol, 1,3-dimethoxy benzene, 1,3-diethoxy benzene, and 1,3-dicyclohexyloxy benzene are preferable, and resorcinol is more preferable. The phenolic compound (A2) may have a linear or branched alkyl group having 1 to 4 carbon atoms, a cyano group, a hydroxyl group, and a halogen or the like, within the range of not deteriorating the effect of the present invention. The phenolic compound (A2) may be used alone or in combination of two or more kinds.

Specific examples of a method for producing the compound represented by the above formula (1) include, but not particularly limited to, the following method. First, 0.1 to 10 moles of the phenolic compound (A2) is reacted per mole of the aldehyde compound (A1) at 20 to 150° C. for about 0.5 to 20 hours in the presence of an acid catalyst (such as hydrochloric acid, sulfuric acid, or para-toluene sulfonic acid) in an organic solvent such as methanol or ethanol. Then, the obtained reaction product can be filtered, washed with alcohols such as methanol, washed with water, filtered to separate, and then dried, to obtain the compound represented by the above formula (1). The compound represented by the above formula (1) can also be obtained by using a basic catalyst (such as sodium hydroxide, barium hydroxide, or 1,8-diazabicyclo[5.4.0]undecene-7) instead of the acid catalyst and reacting in the same way. Furthermore, the compound represented by the above formula (1) can also be produced by treating the above aldehyde compound (A1) with hydrogen halide or halogen gas into dihalide, and reacting the isolated dihalide with the phenolic compound (A2).

Publicly known methods such as separation by a recrystallization method, column chromatography, and preparative liquid chromatography can be employed as a method for isolating the specific stereoisomer (cct body) used in the present embodiment from the reaction product obtained by the above reaction, and a method for obtaining the resist base material containing the stereoisomer as a main component. A method due to optimization of a reaction solvent, reaction temperature, and reaction time or the like upon production can be also employed. These methods may be used in combination of two or more kinds.

In order to reduce the remaining metal amount in the compound represented by the formula (1) (cct body), and to improve the purity, the compound may be purified if required. When an acid catalyst and a co-catalyst remain in the compound represented by the formula (1) (cct body), the storage stability of a resist composition containing a resist base material containing the cct body as a main component generally decreases. When a basic catalyst remains in the compound represented by the formula (1) (cct body), the sensitivity of a resist composition containing a resist base material containing the cct body as a main component generally decreases. Therefore, purification for the purpose of reducing the remaining catalyst may be conducted.

It is possible to arbitrarily select the optimal one for the acid aqueous solution, the basic aqueous solution, the ion exchange resin, and the silica gel column chromatography used for the purification, according to the amount and kind of metal, acidic compound and basic compound to be removed, and the kind of target compound or the like. Examples of the acid aqueous solution include, but not particularly limited to, aqueous solutions of hydrochloric acid, nitric acid, and acetic acid with a concentration of 0.01 to 10 mol/L. Examples of the basic aqueous solution include, but not particularly limited to, an aqueous solution of ammonia with a concentration of 0.01 to 10 mol/L. Examples of the ion exchange resin include, but not particularly limited to, a cation exchange resin. Examples of a commercially available product of the cation exchange resin include, but not particularly limited to, Amberlyst 15J-HG Dry manufactured by Organo.

Drying may be conducted after the purification. Drying can be conducted by a publicly known method. Examples of the method include, but not particularly limited to, methods of vacuum drying, hot air drying, and blast drying under the condition where the compound represented by the formula (1) (and the resist base material containing the compound as a main component) is not modified.

Preferably, the compound represented by the above formula (1) (cct body) can form an amorphous film by spin coating. The compound can be applied to a typical semiconductor production process.

The compound represented by the above formula (1) (cct body) is useful as a negative type resist base material which becomes a hardly soluble compound in a developing solution by being irradiated with KrF excimer laser, extreme ultraviolet, electron beam, or X-ray. This is considered to be because by irradiating the compound with KrF excimer laser, extreme ultraviolet, electron beam, or X-ray, a condensation reaction among the compounds is induced to provide a compound hardly soluble in an alkaline developing solution. A resist pattern thus obtained has very small LER.

The compound represented by the above formula (1) (cct body) can be used as a main component of a negative type resist base material. Moreover, the compound can be added to a resist composition as an additive agent for improving sensitivity and etching resistance, for example. In this case, the amount of the compound represented by the above formula (1) (cct body) added is preferably 1 to 49.999% by mass of the total weight of the solid component of the resist composition.

Resist Composition

The resist composition of the present embodiment contains a resist base material and a solvent. The resist base material contains the compound represented by the above formula (1). A content of the compound represented by the above formula (1) in the resist base material is 50 to 100% by mass.

In the resist composition of the present embodiment, the content of the solvent is preferably 20 to 99% by mass, more preferably 50 to 99% by mass, still more preferably 60 to 98% by mass, and particularly preferably 90 to 98% by mass. In the resist composition of the present embodiment, the content of the component other than the solvent is preferably 1 to 80% by mass, more preferably 1 to 50% by mass, still more preferably 2 to 40% by mass, and particularly preferably 2 to 10% by mass. When the contents of the solvent and component other than the solvent are set to be within the above range, the resist composition easily prepares a solution by the high solubility of the resist base material, and can achieve film thickness control and mixture with various compounds.

Resist Base Material

In the resist composition of the present embodiment, the content of the compound represented by the above formula (1) in the resist base material is within the range of 50 to 100% by mass. When the content of the compound represented by the above formula (1) in the resist base material is set to be within the above range, the resist composition can have high sensitivity, and stably provide a resist pattern having small roughness and a better shape. The content of the compound represented by the above formula (1) in the resist base material is preferably within the range of 55 to 100% by mass, and more preferably within the range of 60 to 100% by mass.

The resist base material used in the present embodiment may contain 50 to 100% by mass of the compound represented by the above formula (1) (cct body). A resist base material obtained by blending the isolated cct body with another stereoisomer or another compound for resists may be used, or the isolated cct body may be independently used as the resist base material. Alternatively, the synthesized cct body containing other stereoisomer without isolating the cct body may be used as the resist base material, as it is.

In the resist composition of the present embodiment, the content of the resist base material is preferably 50.000 to 99.498 parts by mass based on the total content of 100 parts by mass of the component other than the solvent (the total content of the resist base material (A) and optionally used components such as the acid generating agent (C), acid crosslinking agent (G), acid diffusion controlling agent (E), and other component (F)), more preferably 50.000 to 90.000 parts by mass, still more preferably 50.000 to 85.000 parts by mass, and particularly preferably 50.000 to 70.000 parts by mass.

When the content of the resist base material is within above the range, the resist composition has high resolution and small line edge roughness.

Characteristics of Resist Composition

Preferably, the resist composition of the present embodiment can form an amorphous film by spin coating. The dissolution rate of the amorphous film formed by spin coating the resist composition of the present embodiment in a developing solution at 23° C. is preferably 10 angstrom/sec or more, more preferably 10 to 10000 angstrom/sec, and still more preferably 100 to 1000 angstrom/sec. When the dissolution rate is 10 angstrom/sec or more, the amorphous film can dissolve in the developing solution to be a resist. When the dissolution rate is 10000 angstrom/sec or less, the resolution may improve. It is presumed that this is because due to the change in the solubility before and after exposure of the compound represented by the above formula (1), contrast at the interface between the unexposed portion being dissolved in a developing solution and the exposed portion not being dissolved in a developing solution is increased. There are also reduction effects of LER and defect.

Examples of a method for controlling the dissolution rate to be within the above range include, but not particularly limited to, a method for changing the content ratio of the component other than the solvent to control the dissolution rate, and a method for using a dissolution promoting agent and/or a dissolution controlling agent to be described below to control the dissolution rate.

In the present embodiment, the dissolution rate can be obtained by a publicly known method. For example, the dissolution rate can be obtained by measuring a film thickness change in the amorphous film before and after being immersed in the developing solution according to an ellipsometry method or a quartz crystal microbalance method (QCM method).

For the resist composition of the present embodiment, the dissolution rate of the amorphous film after being irradiated with radiation such as KrF excimer laser, extreme ultraviolet, electron beam, or X-ray (the portion exposed by radiation) in a developing solution at 23° C., or the dissolution rate of the amorphous film heated at 20 to 250° C. in a developing solution at 23° C. is preferably 5 angstrom/sec or less, more preferably 0.05 to 5 angstrom/sec, and still more preferably 0.0005 to 5 angstrom/sec. When the dissolution rate is 5 angstrom/sec or less, the amorphous film is insoluble in a developing solution, and can be used for a resist. When the dissolution rate is 0.0005 angstrom/sec or more, the resolution may improve. It is presumed that this is because the micro surface portion of the compound represented by the above formula (1) dissolves and LER is reduced. There is also a reduction effect of defect.

Examples of a method for controlling the dissolution rate to be within the above range include, but not particularly limited to, a method for changing the content ratio of the component other than the solvent to control the dissolution rate, and a method for using a dissolution promoting agent and/or a dissolution controlling agent to be described below to control the dissolution rate.

Acid Generating Agent (C)

The resist composition of the present embodiment preferably contains one or more acid generating agents (C) generating an acid directly or indirectly by irradiation of any one radiation selected from the group consisting of visible light, ultraviolet, excimer laser, electron beam, extreme ultraviolet (EUV), X-ray, and ion beam. In the resist composition of the present embodiment, the content of the acid generating agent (C) is preferably 0.001 to 49 parts by mass based on the total content of 100 parts by mass of the component other than the solvent, more preferably 1 to 40 parts by mass, still more preferably 3 to 30 parts by mass, and particularly preferably 10 to 25 parts by mass. When the content of the acid generating agent (C) is within the above range, the resist composition can provide a pattern profile with high sensitivity and low edge roughness. In the present embodiment, the acid generation method is not limited as long as an acid is generated within a system. By using excimer laser instead of ultraviolet such as g-ray and i-ray, finer processing is possible, and also by using electron beam, extreme ultraviolet, X-ray or ion beam as a high energy ray, further finer processing is possible.

The acid generating agent (C) is preferably at least one kind selected from the group consisting of compounds represented by the following formulae (7-1) to (7-8):

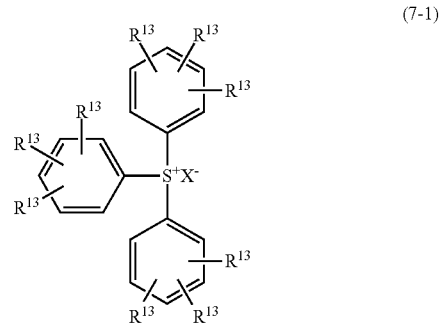

(7-1)

In the formula (7-1), $R^{13}$ may be the same or different, and are each independently a hydrogen atom, a linear, branched or cyclic alkyl group, a linear, branched or cyclic alkoxy group, a hydroxyl group, or a halogen atom; $X^-$ is an alkyl group, an aryl group, a sulfonic acid ion having a halogen substituted alkyl group or a halogen substituted aryl group, or a halide ion.

The compound represented by the above formula (7-1) is preferably at least one kind selected from the group consisting of diphenyltrimethylphenylsulfonium-p-toluenesulfonate triphenylsulfonium trifluoromethanesulfonate, triphenylsulfonium nonafluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium-2-trifluoromethylbenzenesulfonate, diphenyl-2,4,6-trimethylphenylsulfonium-4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium-p-toluenesulfonate, triphenylsulfonium10-camphorsulfonate, diphenyl-4-hydroxyphenylsulfonium10-camphorsulfonate, and cyclo(1,3-perfluoropropanedisulfone)imidate. Above all, the compound represented by the formula (7-1) is more preferably diphenyltrimethylphenylsulfonium-p-toluenesulfonate, triphenylsulfonium-p-toluenesulfonate, triphenylsulfonium trifluoromethanesulfonate, and triphenylsulfonium nonafluoromethanesulfonate.

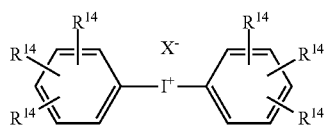

(7-2)

In the formula (7-2), $R^{14}$ may be the same or different, and each independently represents a hydrogen atom, a linear, branched or cyclic alkyl group, a linear, branched or cyclic alkoxy group, a hydroxyl group, or a halogen atom. $X^-$ is the same as $X^-$ in the above formula (7-1).

The compound represented by the above formula (7-2) is preferably at least one kind selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium-4-trifluoromethylbenzenesulfonate, bis(4-t-butylphenyl)iodonium-2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium-2-trifluoromethylbenzenesulfonate, diphenyliodonium-4-trifluoromethylbenzenesulfonate, diphenyliodonium-2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphersulfonate.

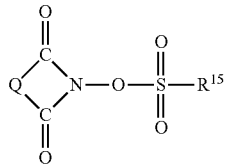

(7-3)

In the formula (7-3), Q is an alkylene group, an arylene group, or an alkoxylene group, and $R^{15}$ is an alkyl group, an aryl group, a halogen substituted alkyl group, or a halogen substituted aryl group.

The compound represented by the above formula (7-3) is preferably at least one kind selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)naphthylimide, N-(n-octanesulfonyloxy)bicyclo[2.2.1]hept-5-en-2,3-dicarboxyimide, N-(n-octanesulfonyloxy)naphthylimide, N-(p-toluenesulfonyloxy)bicyclo[2.2.1]hept-5-en-2,3-dicarboxyimide, N-(p-toluenesulfonyloxy)naphthylimide, N-(2-trifluoromethylbenzenesulfonyloxyl)bicyclo[2.2.1]hept-5-en-2,3-dicarboxyimide, N-(2-trifluoromethylbenzenesulfonyloxyl)naphthylimide, N-(4-trifluoromethylbenzenesulfonyloxyl)bicyclo[2.2.1]hept-5-en-2,3-dicarboxyimide, N-(4-trifluoromethylbenzenesulfonyloxyl)naphthylimide, N-(perfluorobenzenesulfonyloxy)bicyclo[2.2.1]hept-5-en-2,3-dicarboxyimide, N-(perfluorobenzenesulfonyloxy)naphthylimide, N-(1-naphthalenesulfonyloxyl)bicyclo[2.2.1]hept-5-en-2,3-dicarboxyimide, N-(1-naphthalenesulfonyloxyl)naphthylimide, N-(nonafluoro-n-butanesulfonyloxy)bicyclo[2.2.1]hept-5-en-2,3-dicarboxyimide, N-(nonafluoro-n-butanesulfonyloxy)naphthylimide, N-(perfluoro-n-octanesulfonyloxy)bicyclo[2.2.1]hept-5-en-2,3-dicarboxyimide, and N-(perfluoro-n-octanesulfonyloxy)naphthylimide.

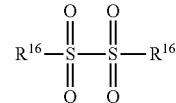

(7-4)

In the formula (7-4), $R^{16}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-4) is preferably at least one kind selected from the group consisting of diphenyldisulfone, di(4-methylphenyl)disulfone, dinaphthyldisulfone, di(4-tert-butylphenyl)disulfone, di(4-hydroxyphenyl)disulfone, di(3-hydroxynaphthyl)disulfone, di(4-fluorophenyl)disulfone, di(2-fluorophenyl)disulfone, and di(4-trifluoromethylphenyl)disulfone.

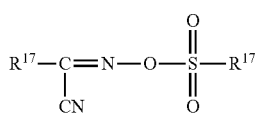

(7-5)

In the formula (7-5), $R^{17}$ may be the same or different, and are each independently an optionally substituted linear, branched or cyclic alkyl group, an optionally substituted aryl group, an optionally substituted heteroaryl group, or an optionally substituted aralkyl group.

The compound represented by the above formula (7-5) is preferably at least one kind selected from the group consisting of α-(methylsulfonyloxyimino)-phenylacetonitrile, α-(methylsulfonyloxyimino)-4-methoxyphenylacetonitrile, α-(trifluoromethylsulfonyloxyimino)-phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

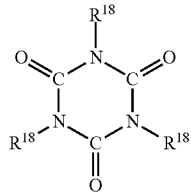

(7-6)

In the formula (7-6), $R^{18}$ may be the same or different, and are each independently a halogenated alkyl group having one or more chlorine atoms and one or more bromine atoms. The number of carbon atoms of the halogenated alkyl group is preferably 1 to 5.

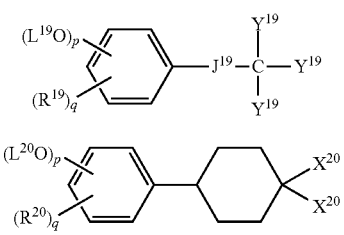

(7-7)

(7-8)

In the formulae (7-7) and (7-8), $R^{19}$ and $R^{20}$ are each independently an alkyl group of 1 to 3 carbon atoms such as a methyl group, an ethyl group, an n-propyl group, and an isopropyl group; a cycloalkyl group such as a cyclopentyl group and a cyclohexyl group; an alkoxyl group of 1 to 3 carbon atoms such as a methoxy group, an ethoxy group, and a propoxy group; or an aryl group such as a phenyl group, a toluoyl group, and a naphthyl group, and preferably an aryl group of 6 to 10 carbon atoms. $L^{19}$ and $L^{20}$ are each independently an organic group having a 1,2-naphthoquinonediazide group. Specifically, preferable examples of the organic group having a 1,2-naphthoquinonediazide group include a 1,2-quinonediazidesulfonyl group such as a 1,2-naphthoquinonediazide-4-sulfonyl group, a 1,2-naphthoquinonediazide-5-sulfonyl group, and a 1,2-naphthoquinonediazide-6-sulfonyl group. Particularly, a 1,2-naphthoquinonediazide-4-sulfonyl group and a 1,2-naphthoquinonediazide-5-sulfonyl group are preferable. p is an integer of 1 to 3; q is an integer of 0 to 4; and $1 \leq p+q \leq 5$. $J^{19}$ is a single bond, a polymethylene group of 1 to 4 carbon atoms, a cycloalkylene group, a phenylene group, a group represented by the following formula (7-7-1), a carbonyl group, an ester group, an amide group, or an ether group. $Y^{19}$ is a hydrogen atom, an alkyl group, or an aryl group, and $X^{20}$ are each independently a group represented by the following formula (7-8-1):

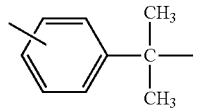

(7-7-1)

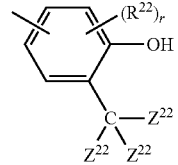

(7-8-1)

In the formula (7-8-1), $Z^{22}$ are each independently an alkyl group, a cycloalkyl group, or an aryl group; $R^{22}$ is an alkyl group, a cycloalkyl group, or an alkoxyl group; and r is an integer of 0 to 3.

Examples of the other acid generating agent include, but not particularly limited to, bissulfonyldiazomethanes such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyl)hexane, and 1,10-bis(cyclohexylsulfonylazomethylsulfonyl)decane; and halogen-containing triazine derivatives such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl)isocyanurate.

Among the above acid generating agents, an acid generating agent having an aromatic ring is preferable, and an acid generating agent represented by the formula (7-1) or (7-2) is more preferable. An acid generating agent, which is a sulfonate ion wherein $X^-$ of the formula (7-1) or (7-2) has an aryl group or a halogen-substituted aryl group, is still more preferable; an acid generating agent, which is a sulfonate ion wherein $X^-$ of the formula (7-1) or (7-2) has an aryl group, is particularly preferable; and diphenyltrimethylphenylsulfonium-p-toluenesulfonate, triphenylsulfonium-p-toluenesulfonate, triphenylsulfonium trifluoromethanesulfonate, and triphenylsulfonium nonafluoromethanesulfonate are particularly preferable. By using the acid generating agent in the resist composition, LER can be further reduced.

The above acid generating agent (C) can be used alone or in combination of two or more kinds.

Acid Crosslinking Agent (G)

The resist composition of the present embodiment preferably contains one or more acid crosslinking agents (G). The acid crosslinking agent (G) is a compound capable of intramolecular or intermolecular crosslinking the compound represented by the above formula (1) in the presence of the acid generated from the acid generating agent (C). Examples of such an acid crosslinking agent (G) include, but not particularly limited to, a compound having one or more groups (hereinafter, also referred to as "crosslinkable group") capable of crosslinking the compound represented by the above formula (1).

Specific examples of such a crosslinkable group include, but not particularly limited to, (i) a hydroxyalkyl group such as a hydroxy (C1-C6 alkyl group), a C1-C6 alkoxy (C1-C6 alkyl group), and an acetoxy (C1-C6 alkyl group), or a group derived therefrom; (ii) a carbonyl group such as a formyl group and a carboxy (C1-C6 alkyl group), or a group derived therefrom; (iii) a nitrogenous group-containing group such as a dimethylaminomethyl group, a diethylaminomethyl group, a dimethylolaminomethyl group, a diethylolaminomethyl group, and a morpholinomethyl group; (iv) a glycidyl group-containing group such as a glycidyl ether group, a glycidyl ester group, and a glycidylamino group; (v) a group derived from an aromatic group such as a C1-C6 allyloxy (C1-C6 alkyl group) and a C1-C6 aralkyloxy (C1-C6 alkyl group) such as a benzyloxymethyl group and a benzoyloxymethyl group; and (vi) a polymerizable multiple bond-containing group such as a vinyl group and a isopropenyl group. As the crosslinkable group of the acid crosslinking agent (G) used in the present embodiment, a hydroxyalkyl group and an alkoxyalkyl group or the like are preferable, and an alkoxymethyl group is particularly preferable.

Examples of the acid crosslinking agent (G) having the above crosslinkable group include, but not particularly limited to, (i) a methylol group-containing compound such as a methylol group-containing melamine compound, a methylol group-containing benzoguanamine compound, a methylol group-containing urea compound, a methylol group-containing glycoluryl compound, and a methylol group-containing phenolic compound; (ii) an alkoxyalkyl group-containing compound such as an alkoxyalkyl group-containing melamine compound, an alkoxyalkyl group-containing benzoguanamine compound, an alkoxyalkyl group-containing urea compound, an alkoxyalkyl group-containing glycoluryl compound, and an alkoxyalkyl group-containing phenolic compound; (iii) a carboxymethyl group-containing compound such as a carboxymethyl group-containing melamine compound, a carboxymethyl group-containing benzoguanamine compound, a carboxymethyl group-containing urea compound, a carboxymethyl group-containing glycoluryl compound, and a carboxymethyl group-containing phenolic compound; (iv) an epoxy compound such as a bisphenol A based epoxy compound, a bisphenol F based epoxy compound, a bisphenol S based epoxy compound, a novolac resin based epoxy compound, a resol resin based epoxy compound, and a poly(hydroxystyrene) based epoxy compound.

As the acid crosslinking agent (G), a compound having a phenolic hydroxyl group, and a compound and resin where the above crosslinkable group is introduced into an acid functional group in an alkali soluble resin to impart crosslinkability can be further used. The introduction rate of the crosslinkable group in that case is adjusted to be preferably 5 to 100 mol %, more preferably 10 to 60 mol %, and more preferably 15 to 40 mol % based on the total acid functional groups in the compound having a phenolic hydroxyl group, and the alkali soluble resin. By having the introduction rate of the crosslinkable group within the above range, the crosslinking reaction sufficiently occurs, and a decrease in the film remaining rate, and swelling phenomena and meandering or the like of a pattern can be avoided, which is preferable.

In the resist composition of the present embodiment, as the acid crosslinking agent (G), an alkoxyalkylated urea compound or resin thereof, or an alkoxyalkylated glycoluryl compound or resin thereof is preferable. Particularly preferable examples of the acid crosslinking agent (G) include compounds represented by the following formulae (8-1) to (8-3) and an alkoxymethylated melamine compound (acid crosslinking agent (G1)).

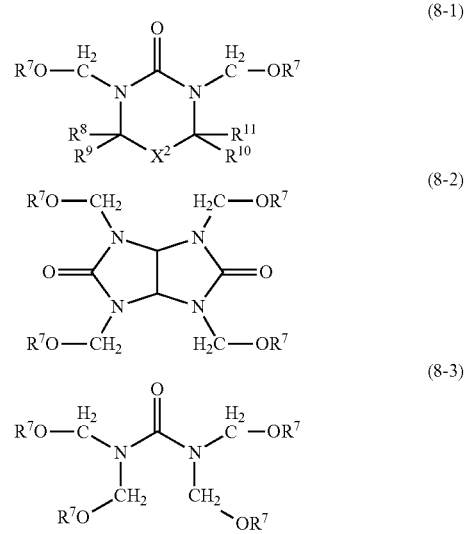

In the above formulae (8-1) to (8-3), $R^7$ each independently represents a hydrogen atom, an alkyl group, or an acyl group; $R^8$ to $R^{11}$ each independently represents a hydrogen atom, a hydroxyl group, an alkyl group, or an alkoxyl group; and $X^2$ represents a single bond, a methylene group, or an oxygen atom.

The number of carbon atoms of the alkyl group represented by $R^7$ is preferably 1 to 6, and more preferably 1 to 3. Examples thereof include, but not particularly limited to, a methyl group, an ethyl group, and a propyl group. The number of carbon atoms of the acyl group represented by $R^7$ is preferably 2 to 6, and more preferably 2 to 4. Examples thereof include, but not particularly limited to, an acetyl group and a propyonyl group. The number of carbon atoms of the alkyl group represented by $R^8$ to $R^{11}$ is preferably 1 to 6, and more preferably 1 to 3. Examples thereof include, but not particularly limited to, a methyl group, an ethyl group, and a propyl group. The alkoxyl group represented by $R^8$ to $R^{11}$ preferably has 1 to 6 carbon atoms, and more preferably 1 to 3 carbon atoms. Examples thereof include, but not particularly limited to, a methoxy group, an ethoxy group, and a propoxy group. $X^2$ is preferably a single bond or a methylene group. $R^7$ to $R^{11}$ and $X^2$ may be substituted with an alkyl group such as a methyl group and an ethyl group, an alkoxy group such as a methoxy group and an ethoxy group, a hydroxyl group, and a halogen atom or the like. A plurality of $R^7$ and $R^8$ to $R^{11}$ may be each the same or different.

Specific examples of the compound represented by the formula (8-1) include, but not particularly limited to, compounds shown below:

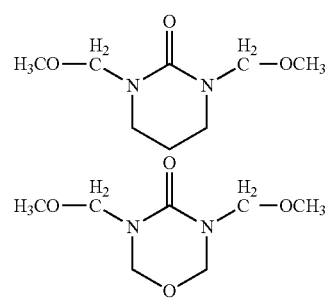

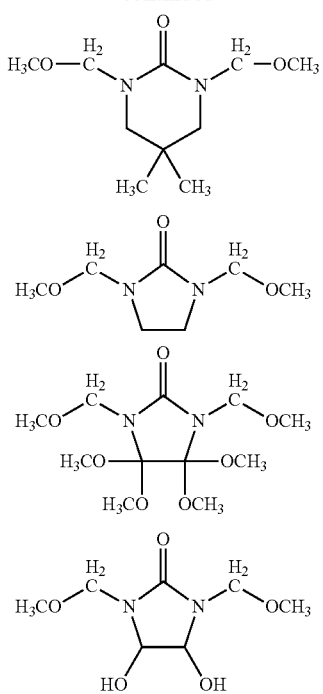

Specific examples of the compound represented by the formula (8-2) include, but not particularly limited to, N,N,N,N-tetra(methoxymethyl)glycoluryl, N,N,N,N-tetra(ethoxymethyl)glycoluryl, N,N,N,N-tetra(n-propoxymethyl)glycoluryl, N,N,N,N-tetra(isopropoxymethyl)glycoluryl, N,N,N,N-tetra(n-butoxymethyl)glycoluryl, and N,N,N,N-tetra(t-butoxymethyl)glycoluryl. Among them, particularly, N,N,N,N-tetra(methoxymethyl)glycoluryl is preferable.

Specific examples of the compound represented by the formula (8-3) include, but not particularly limited to, compounds shown below:

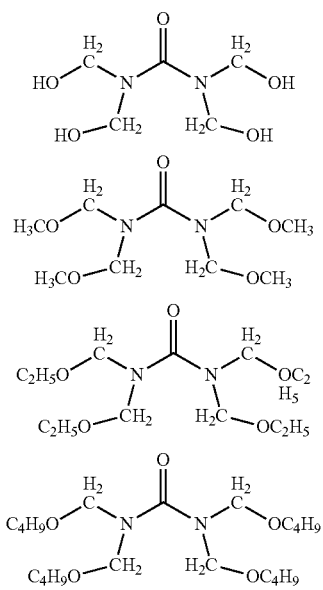

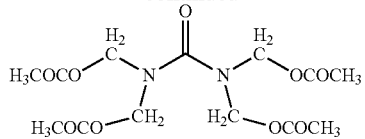

Specific examples of the alkoxymethylated melamine compound include, but not particularly limited to, N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine. Among them, particularly, N,N,N,N,N,N-hexa(methoxymethyl)melamine is preferable.

The above acid crosslinking agent (G1) can be obtained by, for example, but not particularly limited to, conducting a condensation reaction of a urea compound or a glycoluryl compound with formalin to introduce an methylol group, etherifying the product with lower alcohols such as methyl alcohol, ethyl alcohol, propyl alcohol, and butyl alcohol, and then cooling the reaction solution to collect a precipitated compound or resin thereof. The above acid crosslinking agent (G1) can be obtained as a commercially available product such as CYMEL (trade name, manufactured by MT Aqua-Polymer) and NIKALAC (manufactured by Sanwa Chemical).

Other particularly preferable examples of the acid crosslinking agent (G) include a phenol derivative having 1 to 6 benzene rings within a molecule and two or more hydroxyalkyl groups and/or alkoxyalkyl groups within the entire molecule, the hydroxyalkyl groups and/or alkoxyalkyl groups being bonded to any of the above benzene rings (acid crosslinking agent (G2)). As the acid crosslinking agent (G), preferable examples thereof include a phenol derivative having a molecular weight of 1500 or less, 1 to 6 benzene rings and a total of two or more hydroxyalkyl groups and/or alkoxyalkyl groups within a molecule, the hydroxyalkyl groups and/or alkoxyalkyl groups being bonded to any one of the above benzene rings, or a plurality of benzene rings.

As the hydroxyalkyl group bonded to a benzene ring, the hydroxyalkyl group of 1 to 6 carbon atoms such as a hydroxymethyl group, a 2-hydroxyethyl group, and a 2-hydroxy-1-propyl group is preferable. As the alkoxyalkyl group bonded to a benzene ring, the alkoxyalkyl group of 2 to 6 carbon atoms is preferable. Specifically, a methoxymethyl group, an ethoxymethyl group, an n-propoxymethyl group, an isopropoxymethyl group, an n-butoxymethyl group, an isobutoxymethyl group, a sec-butoxymethyl group, a t-butoxymethyl group, a 2-methoxyethyl group, or a 2-methoxy-1-propyl group is preferable.

Among these phenol derivatives, particularly preferable ones are shown below:

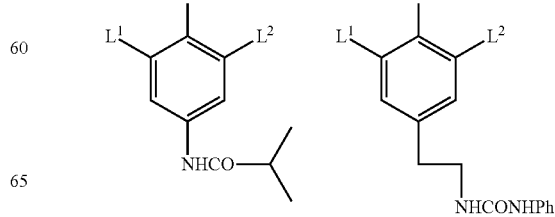

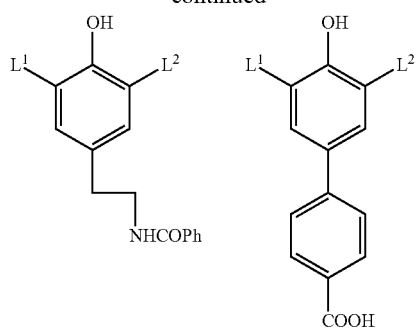
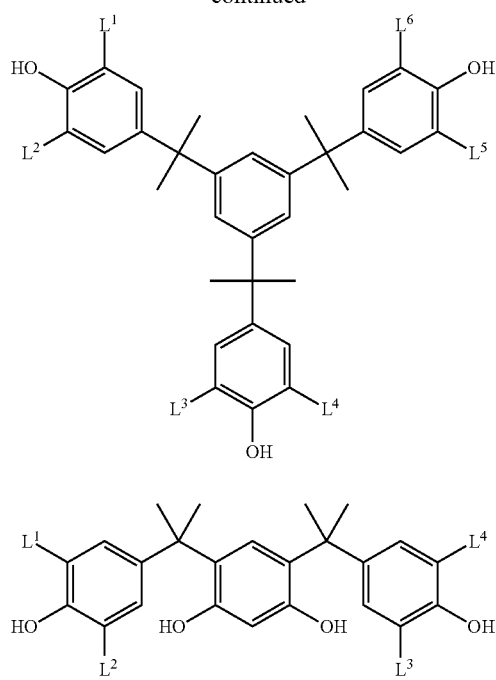
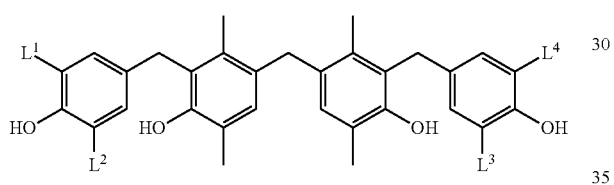
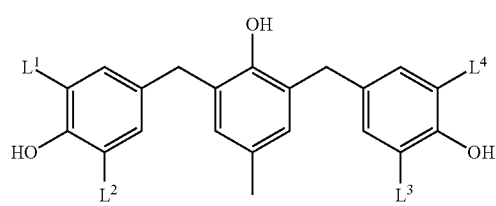
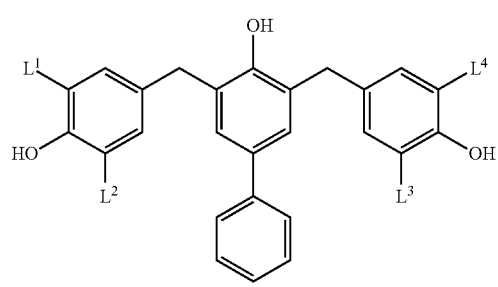
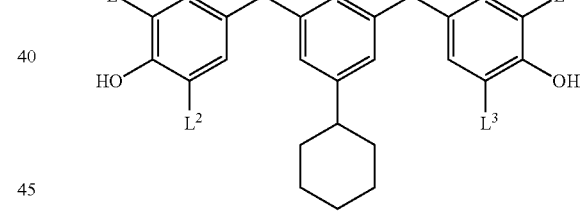
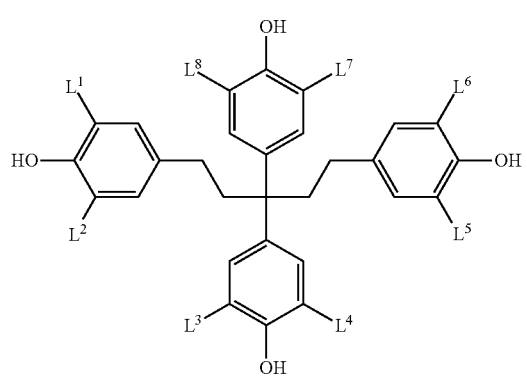
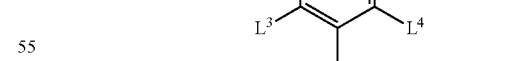
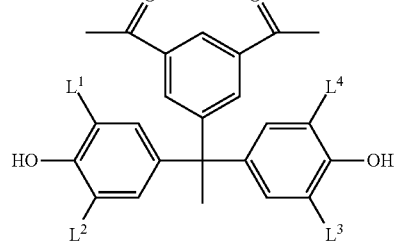

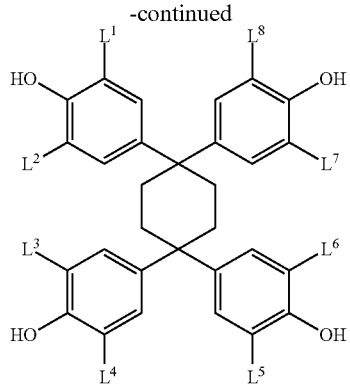
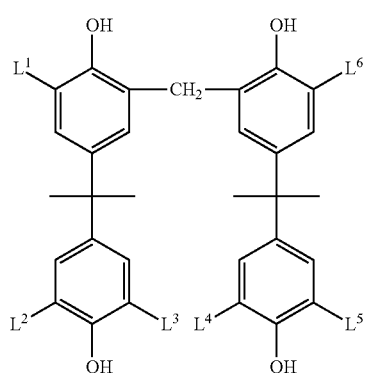
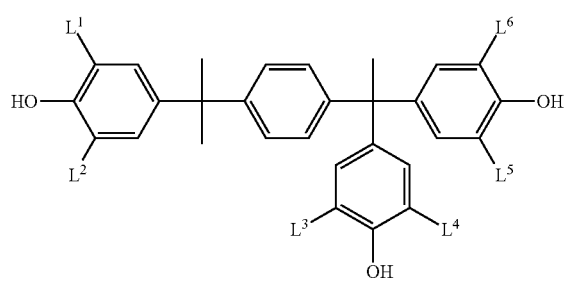
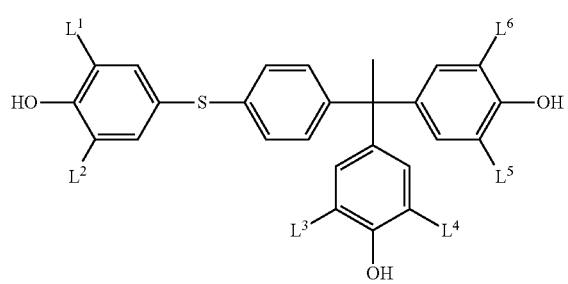
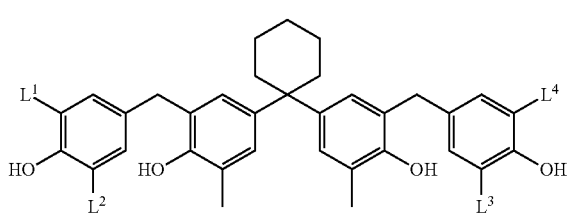
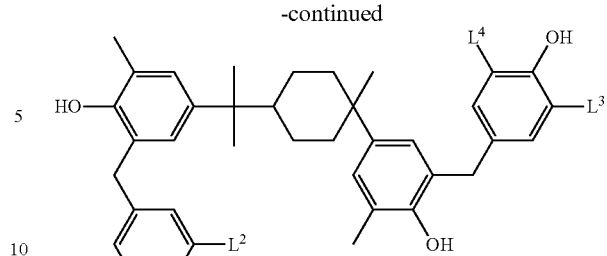
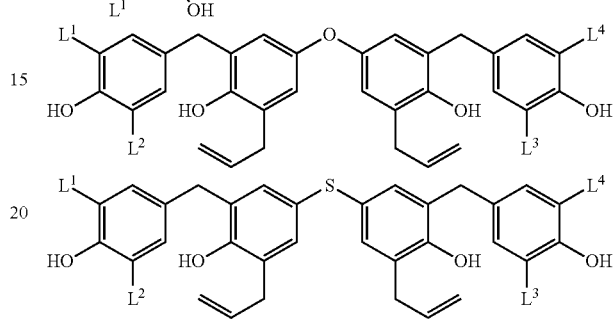
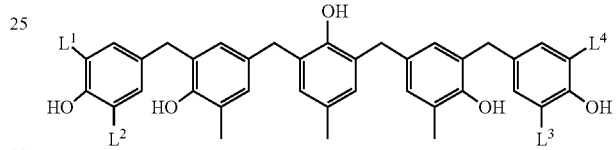
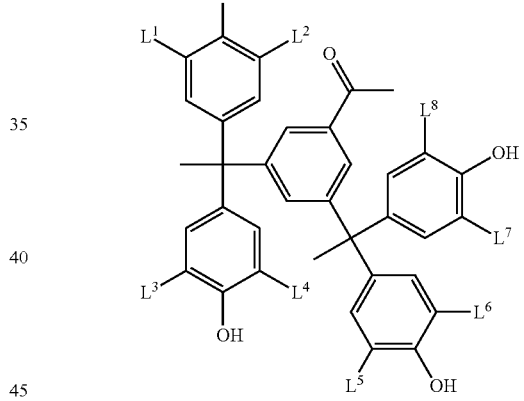
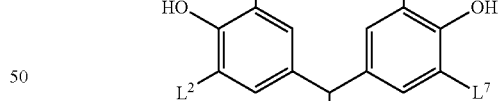
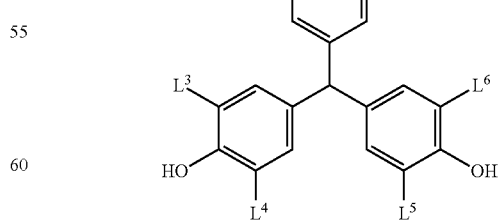
In the above formulae, $L^1$ to $L^8$ may be the same or different, and each independently represents a hydroxymethyl group, a methoxymethyl group, or an ethoxymethyl group. A phenol derivative having a hydroxymethyl group can be obtained by reacting the corresponding phenolic compound having no hydroxymethyl group (a compound where $L^1$ to $L^8$ in the above formulae are a hydrogen atom) with formaldehyde in the presence of a basic catalyst. In this case, in order to prevent resinification and gelation, the reaction temperature is preferably 60° C. or less. Specifically, it can be synthesized by methods described in Japanese Patent Application Laid-Open Nos. 6-282067 and 7-64285 or the like.

A phenol derivative having an alkoxymethyl group can be obtained by reacting the corresponding phenol derivative having a hydroxymethyl group with an alcohol in the presence of an acid catalyst. In this case, in order to prevent resinification and gelation, the reaction temperature is preferably 100° C. or less. Specifically, it can be synthesized by methods described in EP632003A1 or the like.

While the phenol derivative having a hydroxymethyl group and/or an alkoxymethyl group thus synthesized is preferable in terms of stability upon storage, the phenol derivative having an alkoxymethyl group is particularly preferable in terms of stability upon storage. The acid crosslinking agent (G2) may be used alone, or may be used in combination of two or more kinds.

Other particularly preferable examples of the acid crosslinking agent (G) include for example, but not particularly limited to, a compound having at least one α-hydroxyisopropyl group (acid crosslinking agent (G3)). The compound is not particularly limited in the structure, as long as it has an α-hydroxyisopropyl group. A hydrogen atom of a hydroxyl group in the above α-hydroxyisopropyl group may be substituted with one or more acid dissociation groups (R—COO— group, R—SO$_2$— group or the like, wherein R represents a substituent group selected from the group consisting of a linear hydrocarbon group of 1 to 12 carbon atoms, a cyclic hydrocarbon group of 3 to 12 carbon atoms, an alkoxy group of 1 to 12 carbon atoms, a 1-branched alkyl group of 3 to 12 carbon atoms, and an aromatic hydrocarbon group of 6 to 12 carbon atoms). Examples of a compound having the above α-hydroxyisopropyl group include, but not particularly limited to, one kind or two kinds or more of a substituted or non-substituted aromatic based compound, a diphenyl compound, a naphthalene compound, a furan compound or the like containing at least one α-hydroxyisopropyl group. Specific examples thereof include, but not particularly limited to, a compound represented by the following general formula (9-1) (hereinafter, referred to as "benzene based compound (1)"), a compound represented by the following general formula (9-2) (hereinafter, referred to as "diphenyl based compound (2)"), a compound represented by the following general formula (9-3) (hereinafter, referred to as "naphthalene based compound (3)"), and a compound represented by the following general formula (9-4) (hereinafter, referred to as "furan based compound (4)").

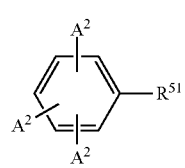

(9-1)

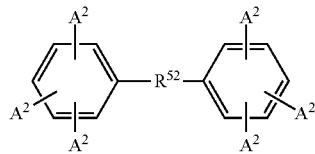

(9-2)

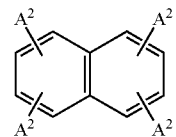

(9-3)

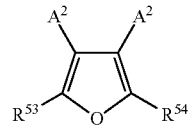

(9-4)

In the above general formulae (9-1) to (9-4), $A^2$ each independently represents an α-hydroxyisopropyl group or a hydrogen atom, and at least one $A^2$ is an α-hydroxyisopropyl group. In the general formula (9-1), $R^{51}$ represents a hydrogen atom, a hydroxyl group, a linear or branched alkylcarbonyl group of 2 to 6 carbon atoms, or a linear or branched alkoxycarbonyl group of 2 to 6 carbon atoms. Furthermore, in the general formula (9-2), $R^{52}$ represents a single bond, a linear or branched alkylene group of 1 to 5 carbon atoms, —O—, —CO—, or —COO—. Also, in the general formula (9-4), $R^{53}$ and $R^{54}$ represent a hydrogen atom or a linear or branched alkyl group of 1 to 6 carbon atoms each independently.

Specific examples of the benzene based compound (1) include, but not particularly limited to, α-hydroxyisopropylbenzenes such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl-alkyl ketones such as 3-α-hydroxyisopropylphenyl-methyl ketone, 4-α-hydroxyisopropylphenyl-methyl ketone, 4-α-hydroxyisopropylphenyl-ethyl ketone, 4-α-hydroxyisopropylphenyl-n-propyl ketone, 4-α-hydroxyisopropylphenyl-isopropyl ketone, 4-α-hydroxyisopropylphenyl-n-butyl ketone, 4-α-hydroxyisopropylphenyl-t-butyl ketone, 4-α-hydroxyisopropylphenyl-n-pentyl ketone, 3,5-bis(α-hydroxyisopropyl)phenyl-methyl ketone, 3,5-bis(α-hydroxyisopropyl)phenyl-ethyl ketone, and 2,4,6-tris(α-hydroxyisopropyl)phenyl-methyl ketone; alkyl 4-α-hydroxyisopropylbenzoates such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Specific examples of the above diphenyl based compound (2) include, but not particularly limited to, α-hydroxyisopropylbiphenyls such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3',4,6,-tetrakis(α-hydroxyisopropyl)biphenyl, 2,4,4',6,-tetrakis(α-hydroxyisopropyl)biphenyl, 3,3',5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;

α-hydroxyisopropyldiphenylalkanes such as 3-α-hydroxyisopropyldiphenylmethane, 4-α-hydroxyisopropyldiphenylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;

α-hydroxyisopropyldiphenyl ethers such as 3-α-hydroxyisopropyldiphenyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4',6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;

α-hydroxyisopropyldiphenyl ketones such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; phenyl α-hydroxyisopropylbenzoates such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, 3,5-bis(α-hydroxyisopropyl)phenyl benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α-hydroxyisopropyl)phenyl benzoate, phenyl 2,4,6-tris(α-hydroxyisopropyl)benzoate, 3-α-hydroxyisopropylphenyl 3,5-bis(α-hydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris(α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Furthermore, specific examples of the above naphthalene based compound (3) include, but not particularly limited to, 1-(α-hydroxyisopropyl)naphthalene, 2-(α-hydroxyisopropyl)naphthalene, 1,3-bis(α-hydroxyisopropyl)naphthalene, 1,4-bis(α-hydroxyisopropyl)naphthalene, 1,5-bis(α-hydroxyisopropyl)naphthalene, 1,6-bis(α-hydroxyisopropyl)naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Specific examples of the above furan based compound (4) include, but not particularly limited to, 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl)furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(α-hydroxyisopropyl)furan.

As the above acid crosslinking agent (G3), a compound having two or more free α-hydroxyisopropyl groups is preferable; the above benzene based compound (1) having two or more α-hydroxyisopropyl groups, the above diphenyl based compound (2) having two or more α-hydroxyisopropyl groups, and the above naphthalene based compound (3) having two or more α-hydroxyisopropyl groups are more preferable; and α-hydroxyisopropylbiphenyls having two or more α-hydroxyisopropyl groups and the above naphthalene based compound (3) having two or more α-hydroxyisopropyl groups are particularly preferable.

The above acid crosslinking agent (G3) can normally be obtained by a method for reacting an acetyl group-containing compound such as 1,3-diacetylbenzene with Grignard reagent such as $CH_3MgBr$ to methylate and then hydrolyzing, or a method for oxidizing an isopropyl group-containing compound such as 1,3-diisopropylbenzene with oxygen or the like to produce a peroxide and then reducing.

The content of the acid crosslinking agent (G) in the resist composition of the present embodiment is preferably 0.5 to 49 parts by mass based on the total content of 100 parts by mass of the component other than the solvent, more preferably 0.5 to 40 parts by mass, still more preferably 1 to 30 parts by mass, and particularly preferably 2 to 20 parts by mass. When the content of the above acid crosslinking agent (G) is the lower limit or more, the inhibiting effect of the solubility of a resist film in an alkaline developing solution can be improved, and a decrease in the film remaining rate, and occurrence of swelling and meandering of a pattern can be inhibited, which is preferable. On the other hand, when the content of the above acid crosslinking agent (G) is the upper limit or less, a decrease in heat resistance as a resist can be inhibited, which is preferable.

The blending ratio of at least one kind of compound selected from the group consisting of the above acid crosslinking agent (G1), acid crosslinking agent (G2), and acid crosslinking agent (G3) in the above acid crosslinking agent (G) is also not particularly limited, and can be within various ranges according to the kind of substrates or the like used upon forming a resist pattern.

In all acid crosslinking agent components, the contents of the above alkoxymethylated melamine compound and/or the compounds represented by (9-1) to (9-3) are 50 to 99% by mass, preferably 60 to 99% by mass, more preferably 70 to 98% by mass, and still more preferably 80 to 97% by mass. By having the contents of the alkoxymethylated melamine compound and/or the compounds represented by (9-1) to (9-3) of 50% by mass or more of all acid crosslinking agent components, the resolution can be improved, which is preferable. By having the contents of the alkoxymethylated melamine compound and/or the compounds represented by (9-1) to (9-3) of 99% by mass or less of all acid crosslinking agent components, the pattern cross section is likely to have a rectangular shape, which is preferable.

Acid Diffusion Controlling Agent (E)

The resist composition of the present embodiment preferably further contains an acid diffusion controlling agent (E). The acid diffusion controlling agent (E) has a function of controlling diffusion of an acid generated from an acid generating agent by radiation irradiation in a resist film to inhibit any unpreferable chemical reaction in an unexposed region or the like. The storage stability of the resist composition is improved by using such an acid diffusion controlling agent (E). Also, along with the improvement of the resolution, the line width change of a resist pattern due to variation in the post exposure delay time before radiation irradiation and the post exposure delay time after radiation irradiation can be inhibited, and the composition has extremely excellent process stability. Examples of such an acid diffusion controlling agent (E) include, but not particularly limited to, a radiation degradable basic compound such as a nitrogen atom-containing basic compound, a basic sulfonium compound, and a basic iodonium compound. The acid diffusion controlling agent (E) can be used alone or in combination of two or more kinds.

Examples of the acid diffusion controlling agent (E) include, but not particularly limited to, a nitrogen-containing organic compound, and a basic compound degradable by exposure. Examples of the nitrogen-containing organic compound include, but not particularly limited to, a compound represented by the following general formula (10):

(hereinafter, referred to as a "nitrogen-containing compound (I)"), a diamino compound having two nitrogen atoms within the same molecule (hereinafter, referred to as a "nitrogen-containing compound (II)"), a polyamino compound or polymer having three or more nitrogen atoms (hereinafter, referred to as a "nitrogen-containing compound (III)"), an amide group-containing compound, a urea compound, and a nitrogen-containing heterocyclic compound. The acid diffusion controlling agent (E) may be used alone as one kind or may be used in combination of two or more kinds.

In the above general formula (10), $R^{61}$, $R^{62}$, and $R^{63}$ represent a hydrogen atom, a linear, branched or cyclic alkyl group, an aryl group, or an aralkyl group each independently. The alkyl group, the aryl group, or the aralkyl group may be non-substituted or may be substituted with a hydroxyl group or the like. Herein, examples of the linear, the branched or the cyclic alkyl group include the one of 1 to 15, and preferably 1 to 10 carbon atoms. Specific examples of the linear, the branched, or the cyclic alkyl group include, but not particularly limited to, a methyl group, an ethyl group, an n-propyl group, an isopropyl group, an n-butyl group, an isobutyl group, a sec-butyl group, a t-butyl group, an n-pentyl group, a neopentyl group, an n-hexyl group, a texyl group, an n-heptyl group, an n-octyl group, an n-ethylhexyl group, an n-nonyl group, and an n-decyl group. Examples of the aryl group include the one of 6 to 12 carbon atoms. Specific examples thereof include, but not particularly limited to, a phenyl group, a tolyl group, a xylyl group, a cumenyl group, and a 1-naphthyl group. Furthermore, examples of the aralkyl group include, but not particularly limited to, the one of 7 to 19, and preferably 7 to 13 carbon atoms. Specific examples thereof include, but not particularly limited to, a benzyl group, an α-methylbenzyl group, a phenethyl group, and a naphthylmethyl group.

Specific examples of the nitrogen-containing compound (I) include, but not particularly limited to, mono(cyclo)alkylamines such as n-hexylamine, n-heptylamine, n-octylamine, n-nonylamine, n-decylamine, n-dodecylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines such as monoethanolamine, diethanolamine, and triethanolamine; and aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Specific examples of the nitrogen-containing compound (II) include, but not particularly limited to, ethylenediamine, N,N,N',N'-tetramethylethylenediamine, N,N,N',N'-tetrakis (2-hydroxypropyl)ethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3- aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Specific examples of the nitrogen-containing compound (III) include, but not particularly limited to, polymers of polyethyleneimine, polyarylamine, and N-(2-dimethylaminoethyl)acrylamide.

Specific examples of the amide group-containing compound include, but not particularly limited to, formamide, N-methylformamide, N,N-dimethylformamide, acetamide, N-methylacetamide, N,N-dimethylacetamide, propioneamide, benzamide, pyrrolidone, and N-methylpyrrolidone.

Specific examples of the urea compound include, but not particularly limited to, urea, methylurea, 1,1-dimethylurea, 1,3-dimethylurea, 1,1,3,3-tetramethylurea, 1,3-diphenylurea, and tri-n-butylthiourea.

Specific examples of the nitrogen-containing heterocyclic compound include, but not particularly limited to, imidazoles such as imidazole, benzimidazole, 4-methylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, amide nicotinate, quinoline, 8-oxyquinoline, and acridine; and pyrazine, pyrazole, pyridazine, quinozaline, purine, pyrrolidine, piperidine, morpholine, 4-methylmorpholine, piperazine, 1,4-dimethylpiperazine, and 1,4-diazabicyclo[2.2.2]octane.

Examples of the radiation degradable basic compound include, but not particularly limited to, a sulfonium compound represented by the following general formula (11-1) and an iodonium compound represented by the following general formula (11-2).

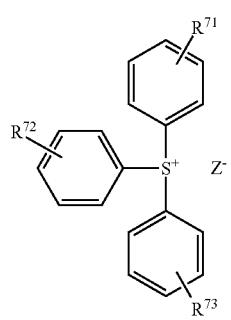

(11-1)

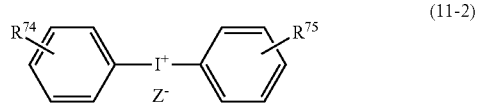

(11-2)

In the above general formulae (11-1) and (11-2), $R^{71}$, $R^{72}$, $R^{73}$, $R^{74}$, and $R^{75}$ represent a hydrogen atom, an alkyl group of 1 to 6 carbon atoms, an alkoxyl group of 1 to 6 carbon atoms, a hydroxyl group, or a halogen atom each independently. Z— represents HO—, R—COO— (R represents an alkyl group of 1 to 6 carbon atoms, an aryl group of 6 to 11 carbon atoms, or an alkaryl group of 7 to 12 carbon atoms), or an anion represented by the following general formula (11-3):

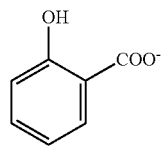

(11-3)

Specific examples of the radiation degradable basic compound include, but not particularly limited to, triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, and 4-t-butylphenyl-4-hydroxyphenyliodonium salicylate.

The content of the acid diffusion controlling agent (E) in the resist composition of the present embodiment is preferably 0.001 to 49 parts by mass based on the total content of 100 parts by mass of the component other than the solvent, more preferably 0.01 to 10 parts by mass, still more preferably 0.01 to 5 parts by mass, and particularly preferably 0.01 to 3 parts by mass. When the content of the acid diffusion controlling agent (E) is within the above range, a decrease in resolution, and deterioration of the pattern shape and the dimension fidelity or the like can be prevented. Moreover, even though the post exposure delay time from electron beam irradiation to heating after radiation irradiation becomes longer, when the content of the acid diffusion controlling agent (E) is within the above range, the shape of the pattern upper layer portion is not deteriorated. When the content of the acid diffusion controlling agent (E) is 10 parts by mass or less, a decrease in sensitivity, and developability of the unexposed portion or the like can be prevented. By using such an acid diffusion controlling agent, the storage stability of a resist composition improves, also along with improvement of the resolution, the line width change of a resist pattern due to variation in the post exposure delay time before radiation irradiation and the post exposure delay time after radiation irradiation can be inhibited, and the composition has extremely excellent process stability.

Other Component (F)

In the resist composition of the present embodiment, within the range of not inhibiting the purpose of the present invention, if required, as the other component (F), one kind or two kinds or more of various additive agents such as a dissolution promoting agent, a dissolution controlling agent, a sensitizing agent, a surfactant, and an organic carboxylic acid or an oxo acid of phosphor, or derivative thereof can be contained.

(1) Dissolution Promoting Agent

A low molecular weight dissolution promoting agent is a component having a function of increasing the solubility of the compound represented by the above formula (1) in a developing solution to moderately increase the dissolution rate of the compound upon developing, when the solubility of the compound is too low. The low molecular weight dissolution promoting agent can be used, within the range of not deteriorating the effect of the present invention. Examples of the above dissolution promoting agent include, but not particularly limited to, a low molecular weight phenolic compound. Specific examples thereof include bisphenols and tris (hydroxyphenyl)methane. These dissolution promoting agents can be used alone or in mixture of two or more kinds.

The content of the dissolution promoting agent in the resist composition of the present embodiment, which is arbitrarily adjusted according to the kind of resist base material to be used, is preferably 0 to 49 parts by mass based on the total content of 100 parts by mass of the component other than the solvent, more preferably 0 to 5 parts by mass, still more preferably 0 to 1 part by mass, and particularly preferably 0 parts by mass.

(2) Dissolution Controlling Agent

The dissolution controlling agent is a component having a function of controlling the solubility of the compound represented by the above formula (1) in a developing solution to moderately decrease the dissolution rate upon developing, when the solubility of the compound is too high. As such a dissolution controlling agent, the one which does not chemically change in steps such as calcination of resist coating, radiation irradiation, and development is preferable.

Examples of the dissolution controlling agent include, but not particularly limited to, aromatic hydrocarbons such as phenanthrene, anthracene, and acenaphthene; ketones such as acetophenone, benzophenone, and phenyl naphtyl ketone; and sulfones such as methyl phenyl sulfone, diphenyl sulfone, and dinaphthyl sulfone. These dissolution controlling agents can be used alone or in two or more kinds.

The content of the dissolution controlling agent in the resist composition of the present embodiment, which is arbitrarily adjusted according to the kind of resist base material to be used, is preferably 0 to 49 parts by mass based on the total content of 100 parts by mass of the component other than the solvent, more preferably 0 to 5 parts by mass, still more preferably 0 to 1 part by mass, and particularly preferably 0 parts by mass.

(3) Sensitizing Agent

The sensitizing agent is a component having a function of absorbing irradiated radiation energy, transmitting the energy to the acid generating agent (C), and thereby increasing the acid production amount, and improving the apparent sensitivity of a resist. Examples of such a sensitizing agent include, but not particularly limited to, benzophenones, biacetyls, pyrenes, phenothiazines, and fluorenes. These sensitizing agents can be used alone or in two or more kinds.

The content of the sensitizing agent in the resist composition of the present embodiment, which is arbitrarily adjusted according to the kind of resist base material to be used, is preferably 0 to 49 parts by mass based on the total content of 100 parts by mass of the component other than the solvent, more preferably 0 to 5 parts by mass, still more preferably 0 to 1 part by mass, and particularly preferably 0 parts by mass.

(4) Surfactant

The surfactant is a component having a function of improving coatability and striation of the resist composition of the present embodiment, and developability of a resist or the like. Such a surfactant may be any of anionic, cationic, nonionic or amphoteric. A preferable surfactant is a nonionic surfactant. The nonionic surfactant has a good affinity with a solvent used in production of resist compositions and more effects. Examples of the nonionic surfactant include, but not particularly limited to, a polyoxyethylene higher alkyl ethers, polyoxyethylene higher alkyl phenyl ethers, and higher fatty acid diesters of polyethylene glycol. Examples of commercially available products of nonionic surfactant include, but not particularly limited to, hereinafter by trade name, EFTOP (manufactured by Jemco Inc.), MEGAFAC (manufactured by DIC Corporation), Fluorad (manufactured by Sumitomo 3M Limited), AsahiGuard, Surflon (hereinbefore, manufactured by Asahi Glass Co., Ltd.), Pepole (manufactured by Toho Chemical Industry Co., Ltd.), KP (manufactured by Shin-Etsu Chemical Co., Ltd.), and Polyflow (manufactured by Kyoeisha Chemical Co., Ltd.).

The content of the surfactant in the resist composition of the present embodiment, which is arbitrarily adjusted according to the kind of resist base material to be used, is preferably 0 to 49 parts by mass based on the total content of 100 parts by mass of the component other than the solvent, more preferably 0 to 5 parts by mass, still more preferably 0 to 1 part by mass, and particularly preferably 0 parts by mass.

(5) Organic Carboxylic Acid or Oxo Acid of Phosphor or Derivative Thereof

For the purpose of prevention of sensitivity deterioration or improvement of a resist pattern shape and post exposure delay stability or the like, and as an additional optional component, the resist composition of the present embodiment can contain an organic carboxylic acid or an oxo acid of phosphor or derivative thereof. The organic carboxylic acid or the oxo acid of phosphor or derivative thereof can be used in combination with the acid diffusion controlling agent, or may be used alone. As the organic carboxylic acid, for example, malonic acid, citric acid, malic acid, succinic acid, benzoic acid, and salicylic acid, or the like are preferable, but not particularly limited to these. Examples of the oxo acid of phosphor or derivative thereof include phosphoric acid or derivative thereof such as ester including phosphoric acid, di-n-butyl ester phosphate, and diphenyl ester phosphate; phosphonic acid or derivative thereof such as ester including phosphonic acid, dimethyl ester phosphonate, di-n-butyl ester phosphonate, phenylphosphonic acid, diphenyl ester phosphonate, and dibenzyl ester phosphonate; and phosphinic acid and derivative thereof such as ester including phosphinic acid and phenylphosphinic acid. Among them, phosphonic acid is particularly preferable.

The organic carboxylic acid or the oxo acid of phosphor or derivative thereof can be used alone or in combination of two or more kinds.

The content of the organic carboxylic acid or the oxo acid of phosphor or derivative thereof in the resist composition of the present embodiment, which is arbitrarily adjusted according to the kind of resist base material to be used, is preferably 0 to 49 parts by mass based on the total content of 100 parts by mass of the component other than the solvent, more preferably 0 to 5 parts by mass, still more preferably 0 to 1 part by mass, and particularly preferably 0 parts by mass.

(6) Other Additive Agent

Furthermore, the resist composition of the present embodiment can contain one kind or two kinds or more of other additive agents other than the above dissolution controlling agent, sensitizing agent, surfactant, and the organic carboxylic acid or the oxo acid of phosphor or derivative thereof, within the range of not inhibiting the purpose of the present invention, if required. Examples of such an additive agent include, but not particularly limited to, a dye, a pigment, and an adhesion aid. For example, the resist composition contains the dye or the pigment, and thereby a latent image of the exposed portion can be visualized and influence of halation upon exposure can be alleviated, which is preferable. The resist composition contains the adhesion aid, and thereby adhesiveness to a substrate can be improved, which is preferable. Furthermore, examples of other additive agent include a halation preventing agent, a storage stabilizing agent, a defoaming agent, and a shape improving agent. Specific examples thereof include 4-hydroxy-4'-methylchalkone.

The total content of the other component (F) in the resist composition of the present embodiment is preferably 0 to 49 parts by mass based on the total content of 100 parts by mass of the component other than the solvent, more preferably 0 to 5 parts by mass, still more preferably 0 to 1 part by mass, and particularly preferably 0 parts by mass.

In the component other than the solvent, the content ratio (% by mass) of the resist base material (A)/acid generating agent (C)/acid crosslinking agent (G)/acid diffusion controlling agent (E)/other component (F) is preferably 50.000 to 99.498/0.001 to 49.000/0.500 to 49.000/0.001 to 49.000/0.000 to 49.000, more preferably 50.000 to 90.000/1.000 to 40.000/0.500 to 40.000/0.010 to 10.000/0.000 to 5.000, still more preferably 50.000 to 85.000/3.000 to 30.000/1.000 to 30.000/0.010 to 5.000/0.000 to 1.000, and particularly preferably 50.000 to 70.000/10.000 to 25.000/2.000 to 20.000/0.010 to 3.000/0.000. The content ratio of each component other than the solvent is selected from each range so that the summation thereof is 100% by mass. When the content ratio of each component other than the solvent is within the above range, the resist composition has excellent performances such as sensitivity, resolution, and developability.

Method for Producing Resist Composition

The method for producing the resist composition of the present embodiment is not particularly limited.

However, the resist composition can be produced, for example, by dissolving the component other than the solvent described above (the resist base material or the like) in a solvent upon use into a homogenous solution, and then if required, filtering through a filter or the like with a pore diameter of about 0.2 μm, for example.

Examples of the solvent used in the production of the resist composition of the present embodiment include, but not particularly limited to, ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers such as ethylene glycol monomethyl ether and ethylene glycol monoethyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers such as propylene glycol monomethyl ether and propylene glycol monoethyl ether; ester lactates such as methyl lactate, ethyl lactate, n-propyl lactate, n-butyl lactate, and n-amyl lactate; aliphatic carboxylic acid esters such as methyl acetate, ethyl acetate, n-propyl acetate, n-butyl acetate, n-amyl acetate, n-hexyl acetate, methyl propionate, and ethyl propionate; other esters such as methyl 3-methoxypropionate, ethyl 3-methoxypropionate, methyl 3-ethoxypropionate, ethyl 3-ethoxypropionate, methyl 3-methoxy-2-methylpropionate, 3-methoxybutylacetate, 3-methyl-3-methoxybutylacetate, butyl 3-methoxy-3-methylpropionate, butyl 3-methoxy-3-methylbutyrate, methyl acetoacetate, methyl pyruvate, and ethyl pyruvate; aromatic hydrocarbon atoms such as toluene and xylene; ketones such as 2-heptanone, 3-heptanone, 4-heptanone, cyclopentanone, and cyclohexanone; amides such as N,N-dimethylformamide, N-methylacetamide, N,N-dimethylacetamide, and N-methylpyrrolidone; and lactones such as γ-lactone. Above all, the solvent is preferably propylene glycol monomethyl ether acetate (PGMEA), propylene glycol monoethyl ether acetate (PGEEA), propylene glycol monomethyl ether (PGME), propylene glycol monoethyl ether (PGEE), cyclohexanone, ethyl lactate, and N-methylpyrrolidone. Such a solvent can provide a coating film containing fewer defects and having a uniform film thickness. The solvent is likely to dissolve the component other than the solvent described above (the resist base material or the like). Furthermore, the solvent has little harmful effect on a human body. These solvents can be used alone or in combination of two or more kinds.

The resist composition of the present embodiment can contain a resin within the range of not inhibiting the purpose of the present invention. Examples of the resin include, but not particularly limited to, a novolac resin; polyvinyl phenols; polyacrylic acid; polyvinyl alcohol; a styrene-maleic anhydride resin; and a polymer containing acrylic acid, vinyl alcohol or vinylphenol as a monomeric unit; or derivative thereof. The content of the resin in the resist composition of the present embodiment, which is arbitrarily adjusted according to the kind of the resist base material to be used, is preferably 30 parts by weight or less per 100 parts by weight of the resist base material, more preferably 10 parts by weight or less, still more preferably 5 parts by weight or less, and particularly preferably 0 part by weight.

(Resist Pattern Production Method)

A resist pattern production method of the present embodiment includes the steps of coating a substrate with the above resist composition, to form a resist film, exposing the resist film, and developing the exposed resist film. The resist pattern can also be produced as an upper layer resist in a multilayer process.

Hereinafter, although a method for producing a resist pattern of the present embodiment will be specifically described, the method for producing the resist pattern of the present embodiment is not limited to the following method. A resist film is formed by coating a conventionally publically known substrate with the above resist composition using a coating means such as spin coating, flow casting coating, and roll coating. The conventionally publically known substrate is not particularly limited. For example, a substrate for electronic components, and the one having a predetermined wiring pattern formed thereon, or the like can be exemplified. More specific examples include, but not particularly limited to, a substrate made of a metal such as a silicon wafer, copper, chromium, iron and aluminum, and a glass substrate. Examples of a wiring pattern material include, but not particularly limited to, copper, aluminum, nickel, and gold. Also if required, the substrate may be a substrate having an inorganic and/or organic film provided thereon. Examples of the inorganic film include, but not particularly limited to, an inorganic antireflection film (inorganic BARC). Examples of the organic film include, but not particularly limited to, an organic antireflection film (organic BARC). A substrate for electronic components, and the one having a predetermined wiring pattern formed thereon, or the like may be subjected to surface treatment with hexamethylene disilazane or the like.

Then, the coated substrate is heated if required. The heating temperatures vary according to the blending composition of the resist composition, or the like, but are preferably 20 to 250° C., and more preferably 20 to 150° C. By heating the substrate, the adhesiveness of resist to a substrate may improve, which is preferable. Then, the resist film is exposed to a desired pattern by any radiation selected from the group consisting of visible light, ultraviolet, excimer laser, electron beam, extreme ultraviolet (EUV), X-ray, and ion beam. The exposure conditions or the like are arbitrarily selected according to the compounding composition of the resist composition, or the like. In the present embodiment, in order to stably form a fine pattern with a high degree of accuracy in exposure, the resist film is preferably heated after radiation irradiation. The heating temperatures vary according to the compounding composition of the resist composition, or the like, but are preferably 20 to 250° C., and more preferably 20 to 150° C.

Next, by developing the exposed resist film in a developing solution, a predetermined resist pattern can be produced. As the developing solution, a solvent having a solubility parameter (SP value) close to that of the compound represented by the above formula (1) to be used is preferably selected. Examples of such a developing solution include, but not particularly limited to, a polar solvent such as a ketone-based solvent, an ester-based solvent, an alcohol-based solvent, an amide-based solvent, or an ether-based solvent; and a hydrocarbon-based solvent, or an alkaline aqueous solution.

Examples of the ketone-based solvent include, but not particularly limited to, 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetyl carbinol, acetophenone, methyl naphthyl ketone, isophorone, and propylene carbonate.

Examples of the ester-based solvent include, but not particularly limited to, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, and propyl lactate.

Examples of the alcohol-based solvent include, but not particularly limited to, an alcohol such as methyl alcohol, ethyl alcohol, n-propyl alcohol, isopropyl alcohol (2-propanol), n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include, but not particularly limited to, dioxane and tetrahydrofuran in addition to the above glycol ether-based solvents.

Examples of the amide-based solvent which can be used include, but not particularly limited to, N-methyl-2-pyrrolidone, N,N-dimethylacetamide, N,N-dimethylformamide, phosphoric hexamethyltriamide, and 1,3-dimethyl-2-imidazolidinone.

Examples of the hydrocarbon-based solvent include, but not particularly limited to, an aromatic hydrocarbon-based solvent such as toluene and xylene; and an aliphatic hydrocarbon-based solvent such as pentane, hexane, octane, and decane.

A plurality of these solvents may be mixed, or the solvent may be mixed the solvent with a solvent other than those described above or water within the range having performance. However, in order to sufficiently exhibit the effect of the present invention, the water content ratio as the whole developing solution is preferably less than 70% by mass, more preferably less than 50% by mass, still more preferably less than 30% by mass, and yet still more preferably less than 10% by mass. Particularly preferably, these solvents are substantially moisture free. That is, the content of the organic solvent in the developing solution is preferable 30% by mass or more and 100% by mass or less based on the total amount of the developing solution, more preferably 50% by mass or more and 100% by mass or less, still more preferably 70% by mass or more and yet still more preferably 100% by mass or less, still more preferably 90% by mass or more and 100% by mass or less, and particularly preferably 95% by mass or more and 100% by mass or less.

Examples of the alkaline aqueous solution include, but not particularly limited to, an alkaline compound such as mono-, di- or tri-alkylamines, mono-, di- or tri-alkanolamines, heterocyclic amines, tetramethyl ammonium hydroxide (TMAH), and choline.

Particularly, the developing solution containing at least one kind of solvent selected from the group consisting of a ketone-based solvent, an ester-based solvent, an alcohol-based solvent, an amide-based solvent, and an ether-based solvent improves resist performance such as resolution and roughness of the resist pattern, which is preferable.

The vapor pressure of the developing solution is preferably 5 kPa or less at 20° C., more preferably 3 kPa or less, and still more preferably 2 kPa or less. The evaporation of the developing solution on the substrate or in a developing cup is inhibited by setting the vapor pressure of the developing solution to 5 kPa or less, to improve temperature uniformity within a wafer surface, thereby resulting in improvement in size uniformity within the wafer surface.

Specific examples of the solvent for the developing solution having a vapor pressure of 5 kPa or less include, but not particularly limited to, a ketone-based solvent such as 1-octanone, 2-octanone, 1-nonanone, 2-nonanone, 4-heptanone, 2-hexanone, diisobutyl ketone, cyclohexanone, methylcyclohexanone, phenylacetone, and methyl isobutyl ketone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, butyl formate, propyl formate, ethyl lactate, butyl lactate, and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an ether-based solvent such as tetrahydrofuran; an amide-based solvent such as N-methyl-2-pyrrolidone, N,N-dimethylacetamide, and N,N-dimethylformamide; an aromatic hydrocarbon-based solvent such as toluene and xylene; and an aliphatic hydrocarbon-based solvent such as octane and decane.

Specific examples of the developing solution having a vapor pressure of 2 kPa or less which is a still more preferable range include, but not particularly limited to, a ketone-based solvent such as 1-octanone, 2-octanone, 1-nonanone, 2-nonanone, 4-heptanone, 2-hexanone, diisobutyl ketone, cyclohexanone, methylcyclohexanone, and phenylacetone; an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxy propionate, 3-methoxy butyl acetate, 3-methyl-3-methoxy butyl acetate, ethyl lactate, butyl lactate, and propyl lactate; an alcohol-based solvent such as n-butyl alcohol, sec-butyl alcohol, tert-butyl alcohol, isobutyl alcohol, n-hexyl alcohol, 4-methyl-2-pentanol, n-heptyl alcohol, n-octyl alcohol, and n-decanol; a glycol-based solvent such as ethylene glycol, diethylene glycol, and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol; an amide-based solvent such as N-methyl-2-pyrrolidone, N,N-dimethylacetamide, and N,N-dimethylformamide; an aromatic hydrocarbon-based solvent such as xylene; and an aliphatic hydrocarbon-based solvent such as octane and decane.

To the developing solution, a surfactant can be added in an appropriate amount, if required. The surfactant is not particularly limited but, for example, an ionic or nonionic fluorine-based and/or silicon-based surfactant can be used. Examples of the fluorine-based and/or silicon-based surfactant include, but not particularly limited to, the surfactants described in Japanese Patent Application Laid-Open Nos. 62-36663, 61-226746, 61-226745, 62-170950, 63-34540, 7-230165, 8-62834, 9-54432, and 9-5988, and U.S. Pat. Nos. 5,405,720, 5,360,692, 5,529,881, 5,296,330, 5,436,098, 5,576,143, 5,294,511, and 5,824,451. The surfactant is preferably a nonionic surfactant. The nonionic surfactant is not particularly limited, but a fluorine-based surfactant or a silicon-based surfactant is more preferably used.

The amount of the surfactant used is preferably 0.001 to 5% by mass based on the total amount of the developing solution, more preferably 0.005 to 2% by mass, and more preferably 0.01 to 0.5% by mass.

The development method is not particularly limited. For example, a method for dipping a substrate in a bath filled with a developing solution for a fixed time (dipping method), a method for raising a developing solution on a substrate surface by the effect of a surface tension and keeping it still for a fixed time, thereby conducting the development (puddle method), a method for spraying a developing solution on a substrate surface (spraying method), and a method for continuously ejecting a developing solution on a substrate rotating at a constant speed while scanning a developing solution ejecting nozzle at a constant rate (dynamic dispense method), or the like may be applied. The time for conducting the pattern development is not particularly limited, but is preferably 10 seconds to 90 seconds.

After the step of developing, a step of stopping the development by replacing the developing solution with another solvent may be practiced.

Furthermore, after the step of developing, a step (rinsing step) of rinsing the resist pattern with a rinsing solution containing an organic solvent is preferably included.

The rinsing solution used in the rinsing step after the step of developing is not particularly limited as long as the rinsing solution does not dissolve the resist pattern cured by crosslinking. For example, a solution containing a general organic solvent or water may be used as the rinsing solution. As the rinsing solution, a rinsing solution containing at least one kind of organic solvent selected from a hydrocarbon-based solvent, a ketone-based solvent, an ester-based solvent, an alcohol-based solvent, an amide-based solvent, and an ether-based solvent is preferably used. More preferably, after the step of development, a step of rinsing the resist pattern by using a rinsing solution containing at least one kind of organic solvent selected from the group consisting of a ketone-based solvent, an ester-based solvent, an alcohol-based solvent and an amide-based solvent is conducted. Still more preferably, after the step of developing, a step of rinsing the resist pattern by using a rinsing solution containing an alcohol-based solvent or an ester-based solvent is conducted. Yet still more preferably, after the step of developing, a step of rinsing the resist pattern by using a rinsing solution containing a monohydric alcohol is conducted. Particularly preferably, after the step of developing, a step of rinsing the resist pattern by using a rinsing solution containing a monohydric alcohol having 5 or more carbon atoms is conducted. The time for rinsing the resist pattern is not particularly limited, but is preferably 10 seconds to 90 seconds.

Herein, examples of the monohydric alcohol used in the rinsing step after the step of developing include, but not particularly limited to, a linear, branched or cyclic monohydric alcohol. Specifically, examples of such monohydric alcohol include, but not particularly limited to, 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, and 4-octanol or the like, and monohydric alcohol having 5 or more carbon atoms is particularly preferable. Examples of monohydric alcohol having 5 or more carbon atoms include, but not particularly limited to, 1-hexanol, 2-hexanol, 4-methyl-2-pentanol, 1-pentanol, and 3-methyl-1-butanol or the like.

A plurality of the rinsing solutions may be mixed, or the rinsing solution may be used in combination with an organic solvent other than those described above.

The water content ratio is preferably 10% by mass or less, more preferably 5% by mass or less, and particularly preferably 3% by mass or less. By setting the water content ratio in the rinsing solution to 10% by mass or less, better development characteristics can be obtained.

The vapor pressure at 20° C. of the rinsing solution used is the rinsing step after the step of developing is preferably 0.05 kPa or more and 5 kPa or less, more preferably 0.1 kPa or more and 5 kPa or less, and further preferably 0.12 kPa or more and 3 kPa or less. By setting the vapor pressure of the rinsing solution to 0.05 kPa or more and 5 kPa or less, the temperature uniformity in the wafer surface is enhanced and moreover, swelling due to permeation of the rinsing solution is further inhibited. As a result, the dimensional uniformity in the wafer surface is further improved.

The rinsing solution may also be used after adding an appropriate amount of a surfactant to the rinsing solution.

In the rinsing step, the wafer after development is rinsed using the organic solvent-containing rinsing solution. The method for rinsing treatment is not particularly limited. However, for example, a method for continuously ejecting a rinsing solution on a substrate spinning at a constant speed (spin coating method), a method for dipping a substrate in a bath filled with a rinsing solution for a fixed time (dipping method), and a method for spraying a rinsing solution on a substrate surface (spraying method), or the like can be applied. Above all, it is preferable to conduct the rinsing treatment by the spin coating method and after the rinsing, spin the substrate at a rotational speed of 2,000 rpm to 4,000 rpm, to remove the rinsing solution from the substrate surface.

After producing the resist pattern, a pattern wiring substrate is obtained by etching. Examples of methods for etching include, but not particularly limited to, a publicly known method such as dry etching using plasma gas, and wet etching with an alkaline solution, a cupric chloride solution, and a ferric chloride solution or the like.

After producing the resist pattern, plating can also be conducted on the resist pattern. Examples of the plating method include, but not particularly limited to, copper plating, solder plating, nickel plating, and gold plating.

The remaining resist pattern after etching can be peeled by an organic solvent. Examples of the organic solvent include, but not particularly limited to, PGMEA (propylene glycol monomethyl ether acetate), PGME (propylene glycol monomethyl ether), and EL (ethyl lactate). Examples of the peeling method include, but not particularly limited to, a dipping method and a spraying method. A wiring substrate having a resist pattern formed thereon may be a multilayer wiring substrate, and may have a small diameter through hole.

The wiring substrate can also be produced by a method for producing a resist pattern, then depositing a metal in vacuum, and subsequently dissolving the resist pattern in a solution, i.e., a liftoff method.

EXAMPLES

Embodiments of the present invention will be more specifically described with reference to examples below. However, the present invention is not limited to these examples. In the following syntheses examples, the structure of each compound was confirmed by $^1$H-NMR measurement.

Synthetic Example 1

Synthesis of (cct) Body of Calix Resorcinarene Derivative 74.3 g (3.71 mol) of anhydrous HF and 50.5 g (0.744 mol) of $BF_3$ were charged to a temperature-controllable autoclave (made of SUS 316L) having an internal capacity of 500 ml and equipped with an electromagnetic stirring device. In the autoclave, the content was stirred and the pressure was increased with carbon monoxide to 2 MPa while the liquid temperature was maintained at −30° C. Thereafter, while the pressure was maintained at 2 MPa and the liquid temperature was maintained at −30° C. in the autoclave, a raw material obtained by mixing 57.0 g (0.248 mol) of 4-cyclohexylbenzene and 50.0 g of n-heptane was fed thereto. After the content was maintained for 1 hour, the content in the autoclave was collected into ice, diluted with benzene, and neutralized to obtain an oily layer. The obtained oily layer was analyzed by gas chromatography for evaluating the reaction performance. The 4-cyclohexylbenzene conversion was 100%, and the 4-cyclohexylbenzaldehyde selectivity was 97.3%.

The target component was isolated from the oily layer by simple distillation and analyzed by gas chromatography mass spectrometry (GC-MS). As a result, the isolated substance had a molecular weight of 188, which was 4-cyclohexylbenzaldehyde (hereinafter, also described as CHBAL) as the target product. $^1$H-NMR of the isolated substance in a deuterated chloroform solvent was measured. The chemical shift value of $^1$H-NMR (δ ppm, TMS standard) was 1.0-1.6 (m, 10H), 2.6 (m, 1H), 7.4 (d, 2H), 7.8 (d, 2H), 10.0 (s, 1H).

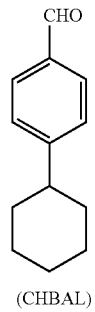

(CHBAL)

Under a nitrogen gas stream, resorcinol manufactured by Kanto Chemical Co., Inc. (16.5 g, 0.15 mol) and ethanol (255 g) were charged to a four necked flask (500 mL) sufficiently dried, substituted with nitrogen, and equipped with a dropping funnel, a Dimroth condenser tube, a thermometer, and a stirring blade, to prepare an ethanol solution. The ethanol solution was cooled with ice. While the ethanol solution was cooled and stirred at 5 to 15° C., concentrated sulfuric acid (97%, 13.9 g, 0.15 mol) and pure water (17.9 g) were dropped in the ethanol solution through the dropping funnel for 10 minutes. Furthermore, the obtained 4-cyclohexylbenzaldehyde (29.7 g, 0.16 mol) and ethanol (26 g) were then dropped, to obtain a mixed solution. Then, the obtained mixed solution was heated to 40° C. by a mantle heater, and stirred for 5 hours for reaction. After the reaction terminated, the obtained reaction liquid was stood to cool, and after it reached room temperature, it was cooled in an ice bath. 1 L of ethyl acetate was added to the cooled reaction liquid, for use as a homogenous solution. Then, the homogenous solution was washed three times with 200 mL of pure water, and washed twice with a saturated sodium chloride solution. Moisture was removed from the washed solution with magnesium sulfate, and ethyl acetate was distilled away, to obtain a reactant. The reactant was vacuum-dried at 40° C., to obtain 38.3 g of a product (hereinafter, referred to as "CR-1a" in some cases).

The product (CR-1a) was analyzed by high-performance liquid chromatography (HPLC). As a result, in the obtained CR-1a, the composition ratio of the (ccc) body/(ctt) body/(cct) body/(tct) body was 18.5/10.1/71.4/0.0.

450 mL of methanol was added to the product (CR-1a), to obtain a solution containing an insoluble matter. The insoluble matter and the solution were separated by filtration. The obtained filtrate was concentrated to obtain 35 g of a concentrate. Furthermore, a mixed solution of ethyl acetate:hexane=100 mL:100 mL was added to the obtained concentrate to obtain a solution containing an insoluble matter. The insoluble matter and the solution were separated by filtration. The obtained filtrate was charged to 500 g of silica gel, and a mixed solution of ethyl acetate:hexane=1/1 to 1/0 was developed, to obtain 9.9 g of a concentrate (hereinafter, referred to as "CR-1b" in some cases) among the obtained concentrate.

The concentrate (CR-1b) was analyzed by high-performance liquid chromatography (HPLC). As a result, in the obtained CR-1b, the composition ratio of the (ccc) body/(ctt) body/(cct) body/(tct) body was 3.7/2.6/93.7/0.0.

The main component of CR-1b was analyzed by gel permeation chromatography (GPC). As a result, in the main component of the obtained CR-1b, the styrene-converted number-average molecular weight Mn was 979, and the weight-average molecular weight Mw was 986. Furthermore, $^1$H-NMR of the main component of CR-1b in a deuterated acetonitrile solvent was measured. The chemical shift value of $^1$H-NMR (δ ppm, TMS standard) was 0.8-1.9 (m, 44H), 5.6, 5.7, 5.7 (m, 4H), 6.2-6.5 (d, 8H), 6.5-7.0 (m, 16H), 7.1 (m, 8H).

From these results, the main component of the obtained CR-1b was identified as a (cct) isomer.

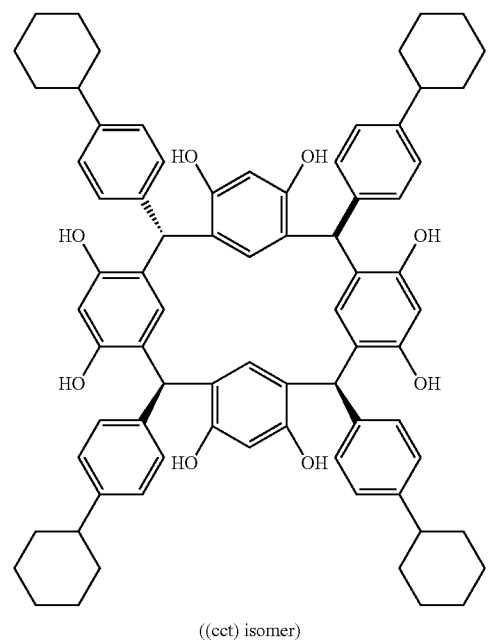 [SMILES: Oc1cc(O)c2cc1[C@H](c1ccc(C3CCCCC3)cc1)c1cc(c(O)cc1O)[C@H](c1ccc(C3CCCCC3)cc1)c1cc(c(O)cc1O)[C@H](c1ccc(C3CCCCC3)cc1)c1cc(c(O)cc1O)[C@H]2c1ccc(C2CCCCC2)cc1]

((cct) isomer)

Synthetic Example 2

Synthesis of (ctt) Body of Calix Resorcinarene Derivative

Under a nitrogen gas stream, resorcinol manufactured by Kanto Chemical Co., Inc. (23.1 g, 0.2 mol) and ethanol (190 g) were charged to a four necked flask (500 mL) sufficiently dried, substituted with nitrogen, and equipped with a dropping funnel, a Dimroth condenser tube, a thermometer, and a stirring blade, to prepare an ethanol solution. The ethanol solution was cooled with ice. While the ethanol solution was cooled and stirred at 5 to 15° C., concentrated sulfuric acid (97%, 18.5 g, 0.2 mol) and pure water (23.9 g) were dropped in the ethanol solution through the dropping funnel for 10 minutes. Furthermore, the obtained 4-cyclohexylbenzaldehyde (37.7 g, 0.2 mol) and ethanol (21 g) were then dropped, to obtain a mixed solution. Then, the obtained mixed solution was heated to 80° C. by a mantle heater, and stirred for 5 hours for reaction. After the reaction terminated, the obtained reaction liquid was stood to cool, and after it reached room temperature, it was cooled in an ice bath. The cooled reaction liquid was left at rest for 1 hour, then a produced light yellow target crude crystal was filtered. The crude crystal was washed three times with 500 mL of methanol, and washed five times with 500 mL of pure water. A solid content was filtered from the washed solution, and vacuum-dried, to obtain 42.5 g of a product (hereinafter, referred to as "CR-2a" in some cases).

The product (CR-2a) was analyzed by high-performance liquid chromatography (hereinafter, also described as "HPLC"). As a result, in the obtained CR-2a, the composition ratio of the (ccc) body/(ctt) body/(cct) body/(tct) body was 49.9/49.9/0.2/0.0.

40 g of the product (CR-2a) was subjected to recrystallization twice with a mixed solution of 8 L tetrahydrofuran/8 L hexane. 11 g of a filtrate concentrate obtained from the second recrystallization was subjected to third recrystallization with 100 mL of ethyl acetate, to obtain 9 g of a crystal substance containing many (ctt) isomers (hereinafter, referred to as "CR-2b" in some cases).

The crystal substance (CR-2b) was analyzed by HPLC. As a result, in the obtained CR-2b, the composition ratio of (ccc) body/(ctt) body/(cct) body/(tct) body was 3.1/96.9/0.0/0.0.

The main component of CR-2b was analyzed by GPC. As a result, in the main component of the obtained CR-2b, the styrene-converted number-average molecular weight Mn was 979, and the weight-average molecular weight Mw was 986. Furthermore, $^1$H-NMR of the main component of CR-2b in a deuterated acetonitrile solvent was measured. The chemical shift value of $^1$H-NMR (δ ppm, TMS standard) was 0.8-1.9 (m, 44H), 5.5 (s, 4H), 6.0-6.4 (d, 8H), 6.6-6.7 (m, 16H), 8.4, 8.5 (m, 8H).

From these results, the main component of the obtained CR-2b was identified as a (ctt) isomer.

some cases). The crystal substance (CR-3a) was analyzed by HPLC. As a result, in the obtained CR-3a, the composition ratio of the (ccc) body/(ctt) body/(cct) body/(tct) body was 97.6/2.4/0.0/0.0.

The main component of CR-3a was analyzed by GPC. As a result, in the main component of the obtained CR-3a, the styrene-converted number-average molecular weight Mn was 979, and the weight-average molecular weight Mw was 986. Furthermore, $^1$H-NMR of the main component of CR-3a in a deuterated acetonitrile solvent was measured. The chemical shift value of $^1$H-NMR (δ ppm, TMS standard) was 0.8-1.9 (m, 44H), 5.6 (s, 4H), 6.1-6.5 (d, 8H), 6.7-6.9 (m, 16H), 8.5 (m, 8H).

From these results, the main component of the obtained CR-3a was identified as a (ccc) isomer.

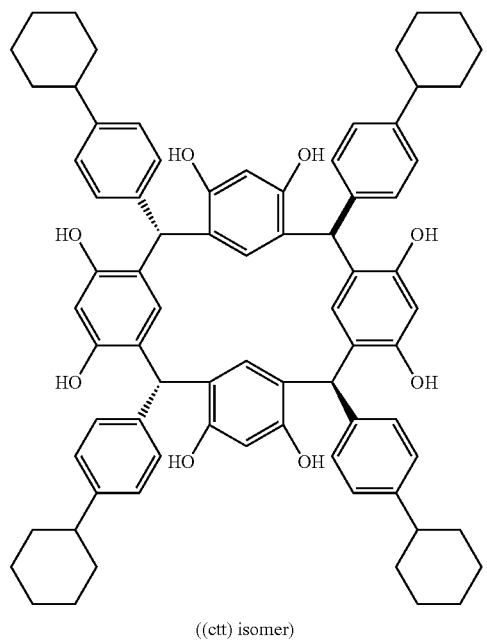 [SMILES: Oc1cc(O)c2cc1[C@H](c1ccc(C3CCCCC3)cc1)c1cc(c(O)cc1O)[C@H](c1ccc(C3CCCCC3)cc1)c1cc(c(O)cc1O)[C@@H](c1ccc(C3CCCCC3)cc1)c1cc(c(O)cc1O)[C@H]2c1ccc(C2CCCCC2)cc1]

((ctt) isomer)

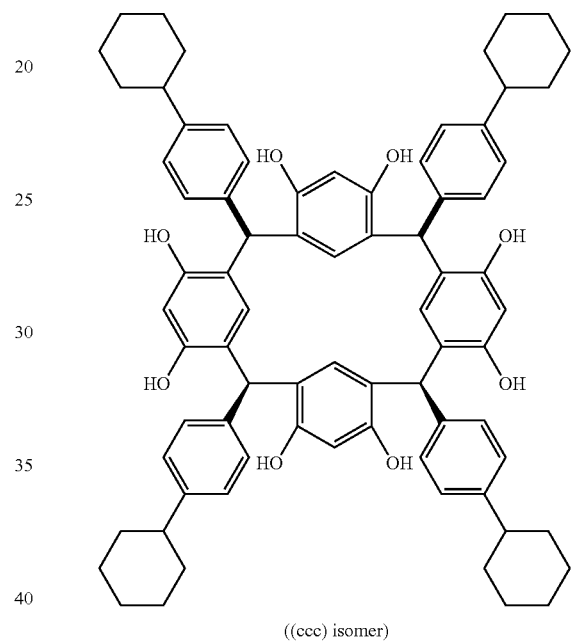

((ccc) isomer)

Synthetic Example 3

Synthesis of (ccc) Body of Calix Resorcinarene Derivative

In the above Synthetic Example 2, 22 g of the crystal substance obtained from the second recrystallization of CR-2a was subjected to third recrystallization with 800 mL of ethyl acetate, to obtain 10 g of a crystal substance containing many (ccc) isomers (hereinafter, referred to as "CR-3a" in Examples 1 to 6 and Comparative Examples 1 to 3

(1) Preparation of Resist Composition

Components were blended into homogenous solutions as described in Table 1. Then, the obtained homogenous solution was filtered through a membrane filter mad of Teflon (registered trademark) with a pore diameter of 0.1 μm, to prepare resist compositions. Each of the prepared resist compositions was evaluated as follows. The evaluation results are shown in Table 2.

TABLE 1

|  | Resist base material (A) (g) | Content of cct body in resist base material (%) | Acid crosslinking agent (G) (g) | Acid generating agent (C) (g) | Acid diffusion controlling agent (E) (g) | Solvent (g) |
|---|---|---|---|---|---|---|
| Example 1 | CR-1b 0.80 | 93.7 | C-1 0.20 | P-1 0.30 | Q-1 0.03 | S-1 43.0 |
| Example 2 | CR-1b 0.80 | 93.7 | C-1 0.20 | P-1 0.20 | Q-1 0.03 | S-1 43.0 |

TABLE 1-continued

|  | Resist base material (A) (g) |  | Content of cct body in resist base material (%) | Acid crosslinking agent (G) (g) | Acid generating agent (C) (g) | Acid diffusion controlling agent (E) (g) | Solvent (g) |
|---|---|---|---|---|---|---|---|
| Example 3 | CR-1a 0.80 |  | 71.4 | C-1 0.20 | P-1 0.30 | Q-1 0.03 | S-1 43.0 |
| Example 4 | CR-1a 0.80 |  | 71.4 | C-1 0.20 | P-1 0.20 | Q-1 0.03 | S-1 43.0 |
| Example 5 | CR-1a 0.72 | CR-2b 0.08 | 64.3 | C-1 0.20 | P-1 0.30 | Q-1 0.03 | S-1 43.0 |
| Example 6 | CR-1a 0.64 | CR-2b 0.16 | 57.1 | C-1 0.20 | P-1 0.20 | Q-1 0.03 | S-1 43.0 |
| Comparative Example 1 | CR-2b 0.80 |  | 0.0 | C-1 0.20 | P-1 0.30 | Q-1 0.03 | S-1 43.0 |
| Comparative Example 2 | CR-2a 1.00 |  | 0.2 | C-1 0.20 | P-1 0.30 | Q-1 0.03 | S-1 30.0 |
| Comparative Example 3 | CR-1a 0.20 | CR-3a 0.60 | 17.9 | C-1 0.20 | P-1 0.20 | Q-1 0.03 | S-1 43.0 |

"P-1," "C-1," "Q-1," and "S-1" in Table 1 are as follows.
Acid Generating Agent (C)
P-1: triphenylbenzenesulfonium trifluoromethanesulfonate (Midori Kagaku Co., Ltd.)
Acid Crosslinking Agent (G)
C-1: NIKALAC MW-100LM (Sanwa Chemical Co., Ltd.)
Acid Diffusion Controlling Agent (E)
Q-1: trioctylamine (Tokyo Kasei Kogyo Co., Ltd.)
Solvent
S-1: propylene glycol monomethyl ether (Tokyo Kasei Kogyo Co., Ltd.)

(2) Patterning Test

A clean silicon wafer was spin coated with the resist composition obtained in the above (1), and then prebaked (PB) before exposure in an oven of 110° C. to form a resist film (amorphous film) with a thickness of 40 nm. The resist film was irradiated with electron beams set to the following three patterns using an electron beam lithography system (ELS-7500 manufactured by ELIONIX INC.).

Pattern 1: a repetitive pattern of a 50 nm straight exposed portion and 50 nm straight unexposed portion Pattern 2: a repetitive pattern of a 40 nm straight exposed portion and 40 nm straight unexposed portion Pattern 3: a repetitive pattern of a 30 nm straight exposed portion and 30 nm straight unexposed portion After irradiation, the resist films were heated at a predetermined temperature (110° C.) for 90 seconds, and immersed in a 2.38% by mass tetramethylammonium hydroxide (TMAH) alkaline developing solution for 60 seconds for development. Subsequently, the resist films were washed with ultrapure water for 30 seconds, and dried to form negative type resist patterns.

Line and space in the obtained resist patterns were observed by a scanning electron microscope (S-4800 manufactured by Hitachi High-Technologies Corporation). A dose amount ($\mu C/cm^2$) in this case was used as sensitivity, and evaluated as follows.

Evaluation Criterion of Sensitivity
1 (excellent sensitivity): dose amount≤45 $\mu C/cm^2$
2 (good sensitivity): 45 $\mu C/cm^2$<dose amount≤60 $\mu C/cm^2$
3 (poor sensitivity): 60 $\mu C/cm^2$<dose amount The line edge roughness (hereinafter, also described as "LER") of the obtained resist pattern was measured as follows. The distance between the edge and the standard line was measured using a Hitachi SEM Terminal PC V5 Offline Length Measuring Software for Semiconductor (manufactured by Hitachi ScienceSystems, Ltd.) for arbitrary 300 points in the length direction (0.75 µm) with 1:1 line and space of the obtained resist pattern, to calculate the standard deviation (3σ) from the measurement results for use as LER.

Evaluation Criterion of LER
A (excellent LER): LER≤5.0 nm
B (good LER): 5.0 nm<LER≤10.0 nm
C (poor LER): 10.0 nm<LER (including a collapse pattern)
D: no pattern

TABLE 2

|  | 50 (nm) | 40 (nm) | 30 (nm) |
|---|---|---|---|
| Example 1 | 1, A | 1, B | 1, B |
| Example 2 | 1, A | 1, A | 1, B |
| Example 3 | 1, A | 1, B | 1, B |
| Example 4 | 1, A | 1, A | 1, B |
| Example 5 | 2, A | 2, A | 2, A |
| Example 6 | 2, A | 2, A | 2, B |
| Comparative Example 1 | 1, C | D | D |
| Comparative Example 2 | 1, A | 1, C | 1, C |
| Comparative Example 3 | 2, A | 2, C | D |

From the above evaluation results, the resist compositions obtained in the present Examples were observed to have sensitivity and LER better than those of the resist compositions obtained in Comparative Examples.

Thus, the resist composition containing the resist base material containing the specific stereoisomer as a main component was found to be able to have high sensitivity, and form a resist pattern having small roughness and a good shape. As long as the requirements of the present embodiment described above are satisfied, the same effect is exhibited also when the compound other than the compound described in Examples is used.

A resist composition containing a specific amount of a specific stereoisomer of the present invention is useful as a resist material, particularly an acid amplification type low molecular resist material, and is suitably used for a resist pattern formation method.

The invention claimed is:
1. A resist composition comprising a resist base material and a solvent,
wherein the resist base material comprises a compound represented by the following formula (1):

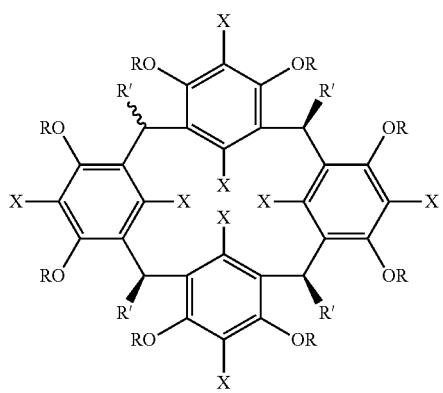

(1)

wherein R are each independently a hydrogen atom, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group having one or more groups selected from the group consisting of a substituted or non-substituted alkylene group, a substituted or non-substituted allylene group, and an ether group;

R' and X are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 20 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 20 carbon atoms, a substituted or non-substituted alkylsilyl group having 1 to 20 carbon atoms, or a group in which each of the groups is bonded to a bivalent group having one or more groups selected from the group consisting of a substituted or non-substituted alkylene group, a substituted or non-substituted allylene group, and an ether group; and directions of three R' to a direction of one R' in a 16-membered plane are cis, cis, and trans directions in order of clockwise rotation, and a content of the compound represented by the formula (1) in the resist base material is 50 to 100% by mass.

2. The resist composition according to claim 1, wherein X is a hydrogen atom, a hydroxyl group, or a substituted or non-substituted alkoxy group having 1 to 20 carbon atoms in the formula (1).

3. The resist composition according to claim 1, wherein, in the formula (1), R' is a group represented by the following formula (2), and X is the hydrogen atom:

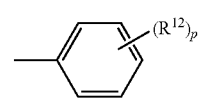

(2)

wherein p is an integer of 0 to 4; and $R^{12}$ are each independently a cyano group, a nitro group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, or a group represented by the following formula (3):

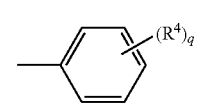

(3)

wherein $R^4$ are each independently a cyano group, a nitro group, a substituted or non-substituted heterocyclic group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, a substituted or non-substituted aryl group having 6 to 14 carbon atoms, a substituted or non-substituted alkoxy group having 1 to 14 carbon atoms, or a substituted or non-substituted alkylsilyl group having 1 to 14 carbon atoms; and q is an integer of 0 to 5.

4. The resist composition according to claim 1, wherein, in the formula (1), R' is a group represented by the following formula (4), and R and X are a hydrogen atom:

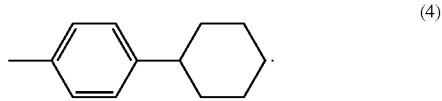

(4)

5. The resist composition according to claim 1, wherein a content of the solvent is 20 to 99% by mass, and a content of a component other than the solvent is 1 to 80% by mass.

6. The resist composition according to claim 1, further comprising an acid generating agent (C) which directly or indirectly generates acid upon exposure to any one radiation selected from the group consisting of visible light, ultraviolet, excimer laser, electron beam, extreme ultraviolet (EUV), X-ray, and ion beam.

7. The resist composition according to claim 1, further comprising an acid crosslinking agent (G).

8. The resist composition according to claim 1, further comprising an acid diffusion controlling agent (E).

9. The resist composition according to claim 1, wherein the component other than the solvent comprises the resist base material (A), an acid generating agent (C), an acid crosslinking agent (G), and an acid diffusion controlling agent (E), and
based on a total content of 100 parts by mass of the component other than the solvent, a content of the resist base material (A) is 50.000 to 99.498 parts by mass; a content of the acid generating agent (C) is 0.001 to 49.000 parts by mass; a content of the acid crosslinking agent (G) is 0.500 to 49.000 parts by mass; and a content of the acid diffusion controlling agent (E) is 0.001 to 49.000 parts by mass.

10. The resist composition according to claim 1, wherein the resist composition can form an amorphous film by spin coating.

11. The resist composition according to claim 10, wherein a dissolution rate of the amorphous film into a developing solution at 23° C. is 10 angstrom/sec or more.

12. The resist composition according to claim 10, wherein a dissolution rate of the amorphous film into a developing solution is 5 angstrom/sec or less after exposed to KrF excimer laser, extreme ultraviolet, electron beam, or X-ray, or after heated at 20 to 250° C.

13. A method for producing a resist pattern, comprising the steps of:
coating a substrate with the resist composition according to claim 1, thereby forming a resist film;
exposing the resist film; and
developing the exposed resist film.

14. A resist base material comprising 50 to 100% by mass of a compound represented by the following formula (1):

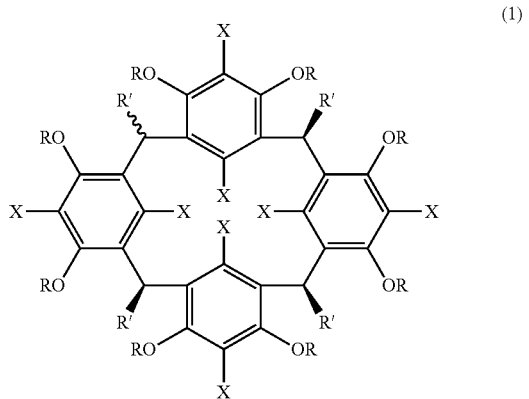

wherein R are each independently a hydrogen atom, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 30 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 30 carbon atoms, a substituted or non-substituted alkylsilyl group having 1 to 20 carbon atoms, or a group in which each of the groups is bonded to a bivalent group having one or more groups selected from the group consisting of a substituted or non-substituted alkylene group, a substituted or non-substituted allylene group, and an ether group;

R' and X are each independently a hydrogen atom, a hydroxyl group, a cyano group, a nitro group, a substituted or non-substituted heterocyclic group, a halogen atom, a substituted or non-substituted linear aliphatic hydrocarbon group having 1 to 20 carbon atoms, a substituted or non-substituted branched aliphatic hydrocarbon group having 3 to 20 carbon atoms, a substituted or non-substituted cyclic aliphatic hydrocarbon group having 3 to 20 carbon atoms, a substituted or non-substituted aryl group having 6 to 20 carbon atoms, a substituted or non-substituted aralkyl group having 7 to 20 carbon atoms, a substituted or non-substituted alkoxy group having 1 to 20 carbon atoms, a substituted or non-substituted amino group having 0 to 20 carbon atoms, a substituted or non-substituted alkenyl group having 2 to 20 carbon atoms, a substituted or non-substituted acyl group having 1 to 20 carbon atoms, a substituted or non-substituted alkoxycarbonyl group having 2 to 20 carbon atoms, a substituted or non-substituted alkyloyloxy group having 1 to 20 carbon atoms, a substituted or non-substituted aryloyloxy group having 7 to 20 carbon atoms, a substituted or non-substituted alkylsilyl group having 1 to 20 carbon atoms, or a group in which each of the groups is bonded to a bivalent group having one or more groups selected from the group consisting of a substituted or non-substituted alkylene group, a substituted or non-substituted allylene group, and an ether group; and directions of three R' to a direction of one R' in a 16-membered plane are cis, cis, and trans directions in order of clockwise rotation.

15. The resist base material according to claim 14, wherein X is a hydrogen atom, a hydroxyl group, or a substituted or non-substituted alkoxy group having 1 to 20 carbon atoms in the formula (1).

16. The resist base material according to claim 14, wherein, in the formula (1), R' is a group represented by the following formula (2), and X is a hydrogen atom:

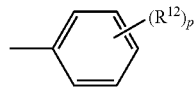 (2)

wherein p is an integer of 0 to 4; and $R^{12}$ are each independently a cyano group, a nitro group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, or a group represented by the following formula (3):

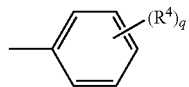 (3)

wherein $R^4$ are each independently a cyano group, a nitro group, a substituted or non-substituted heterocyclic group, a halogen atom, a substituted or non-substituted linear aliphatic hydrocarbon group having 1 to 14 carbon atoms, a substituted or non-substituted branched aliphatic hydrocarbon group having 3 to 14 carbon atoms, a substituted or non-substituted cyclic aliphatic hydrocarbon group having 3 to 14 carbon atoms, a substituted or non-substituted aryl group having 6 to 14 carbon atoms, a substituted or non-substituted alkoxy group having 1 to 14 carbon atoms, or a substituted or non-substituted alkylsilyl group having 1 to 14 carbon atoms; and q is an integer of 0 to 5.

17. The resist base material according to claim 14, wherein, in the formula (1), R' is a group represented by the following formula (4), and R and X are a hydrogen atom:

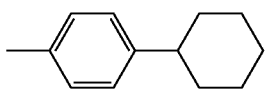 (4)

* * * * *